United States Patent
Houston et al.

[11] Patent Number: 6,010,217
[45] Date of Patent: *Jan. 4, 2000

[54] OPTICALLY CORRECTED SHIELD FOR SAFETY HELMET

[75] Inventors: Malcolm Neal Houston, Foothill Ranch, Calif.; James H. Jannard, Double Island, Wash.; Carlos D. Reyes, Gardnerville, Nev.; Ryan Saylor, Trabucco Canyon, Calif.

[73] Assignee: Oakley, Inc., Foothill Ranch, Calif.

[*] Notice: This patent issued on a continued prosecution application filed under 37 CFR 1.53(d), and is subject to the twenty year patent term provisions of 35 U.S.C. 154(a)(2).

This patent is subject to a terminal disclaimer.

[21] Appl. No.: 08/742,845

[22] Filed: Nov. 1, 1996

Related U.S. Application Data

[63] Continuation-in-part of application No. 08/567,434, Dec. 5, 1995, Pat. No. 5,648,832.

[51] Int. Cl.[7] .............................. G02C 7/02; A41D 13/00
[52] U.S. Cl. ...................... 351/159; 2/9; 351/41
[58] Field of Search ............................ 351/159, 41, 44, 351/177; 2/424, 425, 427, 431, 9, 12

[56] References Cited

U.S. PATENT DOCUMENTS

| | | | |
|---|---|---|---|
| D. 288,980 | 3/1987 | Pernicka | D29/110 |
| D. 349,978 | 8/1994 | Copeland et al. | D29/111 |
| D. 360,488 | 7/1995 | Cardinal | D29/111 |
| D. 365,591 | 12/1995 | Jannard et al. | D16/326 |
| D. 369,375 | 4/1996 | Jannard et al. | D16/326 |
| 1,332,410 | 3/1920 | Potts | 351/177 |
| 1,354,040 | 9/1920 | Hammon | 351/159 |
| 1,536,828 | 5/1925 | Drescher | 351/176 |
| 1,619,341 | 3/1927 | Gagnon | 351/177 |
| 1,697,030 | 1/1929 | Tillyer | 351/159 |
| 1,741,536 | 12/1929 | Rayton | 351/41 |
| 1,910,466 | 5/1933 | Glancy | 351/41 |
| 1,942,400 | 1/1934 | Glancy | 351/41 |
| 2,406,608 | 8/1946 | Joyce | 2/440 |
| 2,442,849 | 6/1948 | Glazer | 351/41 |
| 3,149,632 | 9/1964 | Colley | 128/201.23 |

(List continued on next page.)

FOREIGN PATENT DOCUMENTS

| | | |
|---|---|---|
| 0456321 | 5/1949 | Canada . |
| 0 015 796 A2 | 9/1980 | European Pat. Off. . |
| 0 121 018 A2 | 10/1984 | European Pat. Off. . |
| 0 446 698 A2 | 9/1991 | European Pat. Off. . |
| 2 626 086 | 7/1989 | France . |
| 2 626 683 | 8/1989 | France . |
| 2 688 322 | 9/1993 | France . |
| 2 740 231 | 4/1997 | France . |
| 38 17 850 A1 | 7/1989 | Germany . |
| 1765802A1 | 9/1992 | Switzerland . |
| 2 278 459 | 11/1994 | United Kingdom . |
| 3,162,862 | 12/1964 | Miller ........................... 2/424 |
| 3,223,086 | 12/1965 | Denton ...................... 128/201.24 |
| 3,229,303 | 1/1966 | Jonassen ......................... 2/14 |
| 3,423,758 | 1/1969 | Heacox ......................... 2/424 |
| 3,586,448 | 6/1971 | Beasse ........................ 356/172 |

*Primary Examiner*—Hung Xuan Dang
*Assistant Examiner*—Jordan M. Schwartz
*Attorney, Agent, or Firm*—Knobbe, Martens, Olson & Bear, LLP

[57] ABSTRACT

Disclosed is an optically corrected shield for unitary lens eyeglasses or safety helmets. The shield is characterized by an optical centerline and a mechanical centerline, which intersect each other at an angle. The lens is oriented on the head of the wearer by a frame or helmet that maintains the lens in a position such that the optical centerline is maintained substantially in parallel to the normal sight line of the wearer. Lenses are thus provided which have improved optics when mounted in an as-worn orientation such that they exhibit both vertical "rake" and horizontal "wrap." Methods of making the lenses, and eyewear incorporating the lenses, are also disclosed.

21 Claims, 13 Drawing Sheets

U.S. PATENT DOCUMENTS

| | | | |
|---|---|---|---|
| 3,601,813 | 8/1971 | Aileo | 2/410 |
| 3,806,951 | 4/1974 | Halteman | 2/10 |
| 4,271,537 | 6/1981 | Bowlus et al. | 2/424 |
| 4,271,538 | 6/1981 | Montesi et al. | 2/439 |
| 4,315,335 | 2/1982 | Kennedy, Jr. et al. | 2/424 |
| 4,443,893 | 4/1984 | Yamamoto | 2/436 |
| 4,446,576 | 5/1984 | Hisataka | 2/425 |
| 4,498,202 | 2/1985 | Yamamoto | 2/424 |
| 4,515,448 | 5/1985 | Tackles | 351/41 |
| 4,613,217 | 9/1986 | Fuerter et al. | 351/176 |
| 4,736,466 | 4/1988 | Kallstrom | 2/9 |
| 4,737,918 | 4/1988 | Langlois et al. | 364/474.06 |
| 4,741,611 | 5/1988 | Burns | 351/44 |
| 4,761,315 | 8/1988 | Logan et al. | 351/159 |
| 4,859,048 | 8/1989 | Jannard | 351/159 |
| 4,867,550 | 9/1989 | Jannard | 351/47 |
| 5,050,979 | 9/1991 | Shinohara | 351/159 |
| 5,056,156 | 10/1991 | Kosmo et al. | 2/411 |
| 5,131,101 | 7/1992 | Chin | 2/424 |
| 5,208,614 | 5/1993 | Jannard | 351/159 |
| 5,220,689 | 6/1993 | Miller | 2/12 |
| 5,287,562 | 2/1994 | Rush, III | 2/413 |
| 5,347,323 | 9/1994 | Wilson | 351/44 |
| 5,390,369 | 2/1995 | Tubin | 2/12 |
| 5,412,814 | 5/1995 | Pernicka et al. | 2/424 |
| 5,541,674 | 7/1996 | Jannard | 351/41 |
| 5,555,038 | 9/1996 | Conway | 351/159 |
| 5,648,832 | 7/1997 | Houston et al. | 351/159 |
| 5,689,323 | 11/1997 | Houston et al. | 351/41 |

LINE OF SIGHT

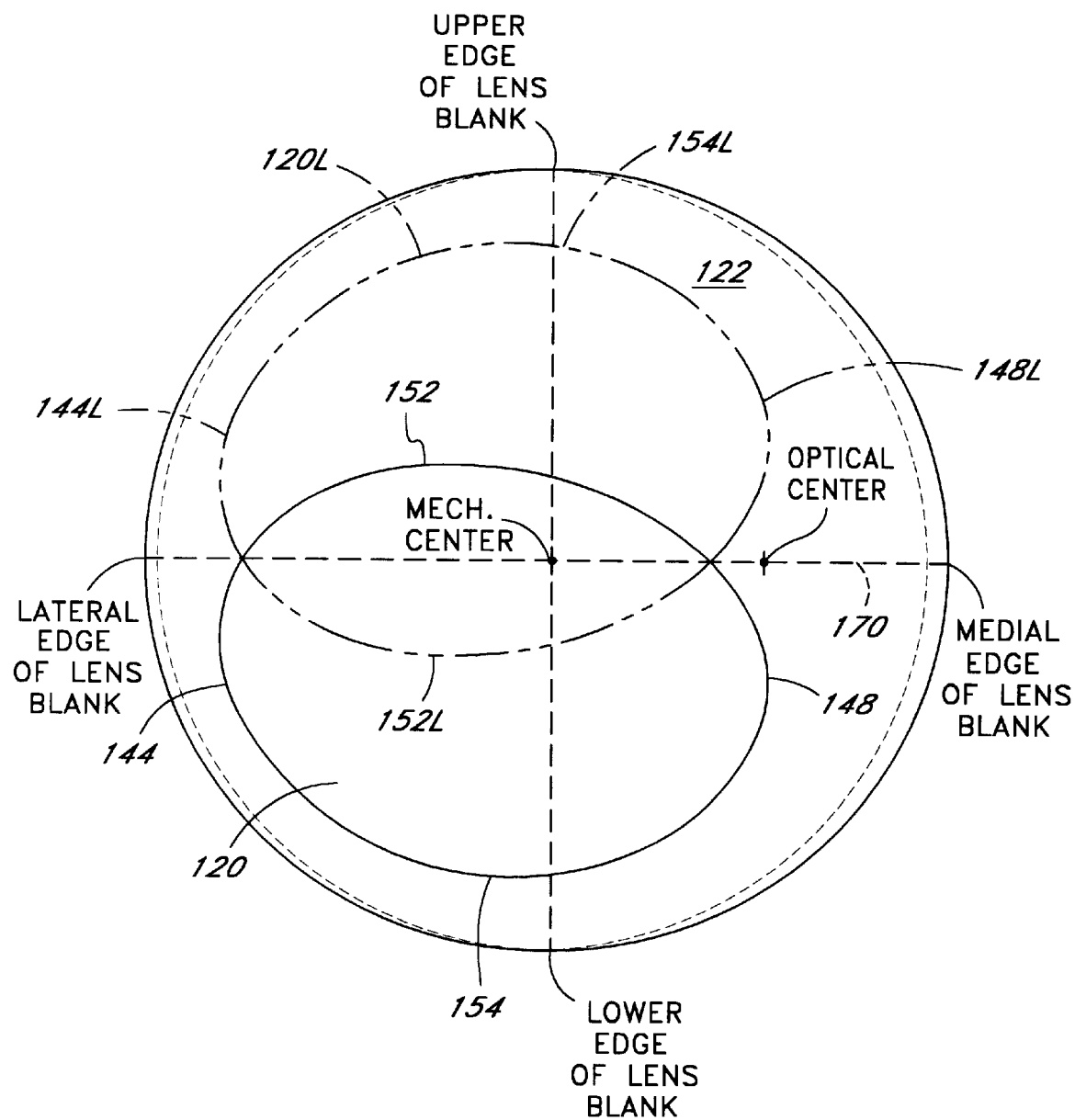

OPTICALLY CORRECTED SHIELD FOR SAFETY HELMET

CROSS-REFERENCE TO RELATED APPLICATION

The present application is a continuation-in-part of the U.S. patent application entitled "DECENTERED NON-CORRECTIVE LENS FOR EYEWEAR," having Ser. No. 08/567,434, filed Dec. 5, 1995, now U.S. Pat. No. 5,648,832 and assigned to the assignee of the present application.

FIELD OF THE INVENTION

The present invention relates generally to lenses used in eyewear, and more particularly to a unitary eye shield configured and oriented to reduce optical distortion as mounted in a safety helmet.

BACKGROUND OF THE INVENTION

A wide variety of improvements have been made in recent years in the eyewear field, particularly with respect to eyewear intended for use in active sports or as fashion sunglasses. These improvements have been incorporated into eyewear having a unitary lens, such as the "Blades®" design (Oakley, Inc.) the "M Frame®" line (Oakley, Inc.), and the "Zero®" line also produced by Oakley, Inc. These eyewear designs accomplish a variety of functional advantages, such as maximizing interception of peripheral light, reducing optical distortion and increasing the wearer's comfort level, compared to previous active sport eyewear.

The unitary lens of the "Blades®" eyewear incorporates the cylindrical geometry disclosed, for example, in U.S. Pat. No. 4,859,048, issued to Jannard. This geometry allows the lens to closely conform to the wearer's face and intercept light, wind, dust, etc. from directly in front of the wearer (anterior direction) and peripherally (lateral direction). See also U.S. Pat. No. 4,867,550 to Jannard (toroidal lens geometry).

Although the early unitary lens systems provided a full side-to-side range of vision and good lateral eye protection, the potential for optical distortion still exists. In a unitary lens system, for example, the angle of incidence from the wearer's eye to the posterior lens surface changes as the wearer's sight line turns in either the vertical or horizontal planes. This results in disparate refraction between light entering closer to the front of the lens and peripheral light entering at the lateral ends. To address this source of prismatic distortion, U.S. Pat. No. 4,859,048 discloses tapering the thickness of the lens from the medial portion toward the lateral edge.

Unitary lens goggles and protective helmet shields are subject to the same sources of optical distortion. A wide variety of goggle and helmet shields are known for such activities as motorcycle riding, skiing, football, lacrosse, hockey and the like. Unitary lenses are also found in underwater diving masks and a variety of industrial safety applications such as welding and for power equipment operators. While the state of the art in each of these applications has generally achieved the desired level of physical eye protection, the current products generally still exhibit relatively high prismatic distortion and sometimes also power and/or astigmatism.

Thus, there remains a need for a nonprescription shield for use in such applications as unitary lens eyeglasses and athletic safety helmets which can intercept light throughout both a vertical and horizontal angular range of vision while at the same time minimize optical distortion throughout that range.

SUMMARY OF THE INVENTION

There is provided in accordance with one aspect of the present invention protective eyewear, such as may be utilized in football helmets, motorcycle helmets, ski goggles, sunglasses and the like. The eyewear comprises a shield support for mounting on the head of a wearer and for positioning a shield across the wearer's normal straight ahead line of sight. A transparent unitary shield is attached to the support. The shield has in a vertical plane an upper limit, a lower limit and a centerpoint halfway therebetween. A mechanical centerline extends through the shield at the centerpoint, the mechanical centerline extending at a perpendicular to a tangent to the surface of the shield at said point. The shield has a front surface which conforms in a vertical plane to portion of a first circle having a first center and the shield has a rear surface which conforms in the vertical plane to a portion of a second circle having a second center. The first and second centers are noncoincident, and lie on an optical centerline which extends through the shield. The support is configured to maintain the shield in the wearer's field of vision in an orientation such that any angle between the optical centerline and the wearer's straight ahead normal line of sight is less than the angle between the optical centerline and the mechanical centerline.

In accordance with another aspect of the present invention, there is provided a method of orienting a shield in a support for holding the shield in a wearer's field of vision. The method comprises the steps of providing a support for holding a shield in the wearer's field of vision, the support configured to maintain the shield in a predetermined relationship with respect to the wearer's theoretical straight ahead line of sight. The support may comprise a safety helmet, a goggle such as a ski goggle, or an eyeglass frame. A shield is provided, which has in at least a vertical plane an optical centerline and a mechanical centerline. The shield is mounted to the support with rake and such that any angle between the optical centerline and the theoretical straight ahead line of sight is no more than about 4°. Preferably, the angle is no more than about 2°, and more preferably, the angle is no more than about 1°.

In accordance with a further aspect of the present invention, there is provided a safety helmet such as for use in football. The safety helmet comprises a helmet configured to be worn on the head of a wearer, and an optical shield supported by the helmet in an orientation that intercepts the wearer's normal straight ahead line of sight. The shield may be directly mounted to the helmet or indirectly mounted such as by attachment to a protective grill which is in turn attached to the helmet. The shield is characterized by an optical centerline, and the shield is maintained by the helmet in an orientation with respect to the wearer's theoretical normal straight ahead line of sight such that the optical centerline deviates by no more than about 10° from the wearer's theoretical straight ahead line of sight.

In accordance with a further aspect of the present invention, there is provided a lens blank for cutting lenses for eyeglass. The lens blank comprises a unitary lens blank having an upper edge and a lower edge and a mechanical centerline extending through the lens blank half way therebetween. The lens blank is provided with an arcuate cross-sectional configuration along a central horizontal plane having a radius r1, and an arcuate cross-sectional configuration along a central vertical plane having a radius r2. R1 is in the range of from about 2 inches to about 4 inches and r2 is greater than or equal to about 1.1 (R1). The lens blank is characterized by an optical centerline extending therethrough, wherein the optical centerline is angularly displaced from the mechanical centerline.

Further features and advantages of the present invention will become apparent from the detailed description of preferred embodiments which follows, when considered together with the attached claims and drawings.

BRIEF DESCRIPTION OF THE DRAWINGS

FIG. 10A illustrates the profile of a properly configured and oriented lens for use in an eyeglass having downward rake, in accordance with a preferred embodiment of the present invention.

FIG. 10B illustrates the profile of a centrally oriented lens with no rake.

FIG. 10C illustrates a lens exhibiting downward rake but which is not configured and oriented to minimize prismatic distortion for the straight ahead line of sight.

FIG. 10D illustrates a prior art orientation of a shield in a football helmet having upward rake, in which the optical centerline and mechanical centerline of the shield are coincident with each other, and are angled in an upward direction with respect to the normal straight ahead line of sight.

FIG. 10E illustrates a shield oriented in a football helmet in accordance with the present invention, in which the optical centerline of the lens is generally parallel to the straight ahead normal line of sight, while the mechanical centerline of the lens is inclined at an angle with respect to the normal line of sight.

FIG. 12A is a top plan view, like that of FIG. 12, additionally showing the position from which a left lens could have been cut from the same lens blank.

DETAILED DESCRIPTION OF THE PREFERRED EMBODIMENTS

Although the preferred embodiments will be discussed below in terms of lenses having "spherical" front and rear surfaces (surfaces which conform substantially to a portion of the surface of a sphere), it will be understood by those having ordinary skill in the art that the invention may also be applicable to lenses having different surface geometries. Additionally, it will be understood that the present invention has application to lenses of many front elevational shapes and orientations in the as worn position beyond those illustrated herein.

Figure 1:
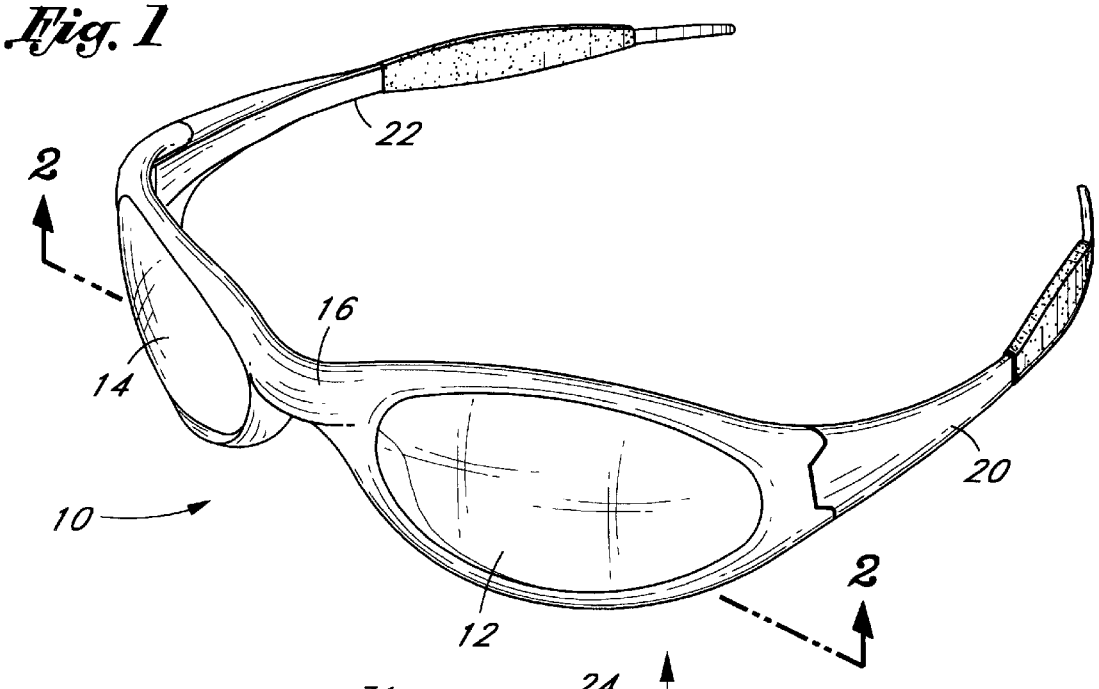
FIG. 1 is a perspective view of eyewear incorporating taper corrected lenses made in accordance with an embodiment of the present invention.
Figure 2:
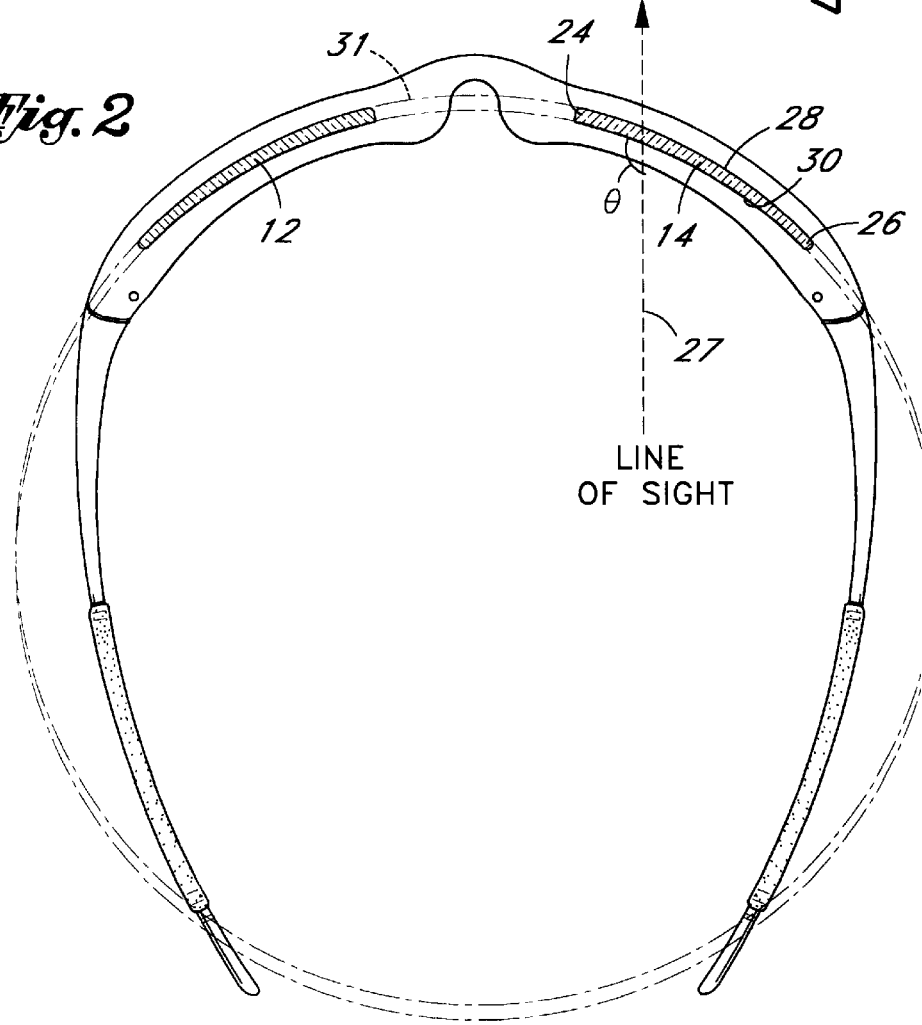
FIG. 2 is a cross-sectional view taken along the lines 2—2 of FIG. 1.

Referring to FIGS. 1 and 2, there is illustrated an eyeglass 10, such as a sunglass having first and second lenses 12, 14 constructed in accordance with an embodiment of the present invention. Although the invention is illustrated in the context of an eyeglass design marketed by Oakley under the Eye Jackets™ name, the present invention relates solely to the lens curvature, taper, and orientation on the head of the wearer. Therefore the particular lens shape revealed in FIG. 1 is not critical to the invention. Rather, lenses of many other shapes and configurations may be constructed which incorporate the configuration and orientation of the present invention, as will become apparent based upon the disclosure herein.

Similarly, the mounting frame 16 having continuous orbitals is not essential to the present invention. The orbitals may bound only the bottom edge(s) of the lenses 12, 14, only the top edges, or the entire lenses as illustrated. Alternatively, the frame 16 can bound any other portions of the lenses as will be evident to those of skill in the art. Frameless eyeglasses can also be constructed in accordance with the present invention, as long as the lens orientation on the head of the wearer is substantially maintained in a predetermined relationship to a preselected sight line as will be discussed below. Preferably, though, the lenses 12, 14 are each mounted in an annular orbital as shown.

A pair of earstems 20, 22 pivotally attach to the frame 16. Alternatively, the earstems 20, 22 may attach directly to the lenses 12, 14. The frame may comprise any of a variety of metals, composites or relatively rigid, molded thermoplastic materials which are well known in the art, and may be transparent or any of a variety of colors. Injection molding, machining and other construction techniques are well known in the art.

Lenses in accordance with the present invention can be manufactured by any of a variety of processes well known in the art.

Typically, high optical quality lenses are cut from a preformed injection molded lens blank. Since the right and left lenses are preferably mirror images of each other, only the right lens will generally be described for most of the discussion below. In describing a method of cutting lenses from preformed lens blanks, however, the manner in which a left lens differs from the right lens will be related to the degree of rake and wrap chosen for the as worn lens orientation. Alternatively, the lens can be molded directly into its final shape and size, to eliminate the need for post molding cutting steps.

Preferably, the lens, or the lens blank from which it is cut, is injection molded and comprises a relatively rigid and optically acceptable material, such as polycarbonate. Other polymeric lens materials can also be used, such as CR-39 and a variety of high index plastics which are known in the art. The decentered taper correction of the present invention may also be applicable to glass lenses, although the need for correction in the present context is generally more pronounced in currently popular nonglass materials.

If the lens is to be cut from a lens blank, the taper and curvature of a carefully preselected portion of the lens blank is transferred to the lens in accordance with a preferred orientation process described below. Preferably, the frame is provided with a slot or other attachment structure that cooperates with the molded curvature of the lens to minimize deviation from, and even improve retention of the as-molded curvature.

Alternatively, the lens or lens blank can be stamped or cut from generally planar tapered sheet stock and then bent into the curved configuration in accordance with the present invention. This curved configuration can then be maintained by the use of a relatively rigid, curved frame, or by heating the curved sheet to retain its curved configuration, as is well known in the thermoforming art.

Most preferably, the curvature of both surfaces of the lens are created in the lens blank molding and polishing processes, and the lens shape is cut from the blank in accordance with the invention as described below.

Referring to FIG. 2, the lens 14 of the present invention is characterized in a horizontal plane by a generally arcuate shape, extending from a medial edge 24 throughout at least a portion and preferably substantially all of the wearer's range of vision to a lateral edge 26. The arc length of the lens from the medial edge 24 to the lateral edge 26 in a dual lens system will generally be within the range of from about 1½ inches to about 3½ inches, and preferably within the range of from about 2 inches to about 3 inches. In one preferred embodiment, the arc length of the lens is about 2⅜ inches.

Although the outer surfaces of the lenses 12, 14 appear to be illustrated as lying on a common circle 31, the right and left lenses in a high wrap eyeglass will generally be canted such that the medial edge of each lens will fall outside of the circle 31 and the lateral edges will fall inside of the circle 31. Such canting of the lens increases the angle θ (FIG. 2) and increases the desirability of the optical correction achieved by the present invention.

When worn, the lens 14 should at least extend across the wearer's normal straight ahead line of sight 27, and preferably substantially across the wearer's peripheral zones of vision. As used herein, the wearer's normal line of sight shall refer to a line projecting straight ahead of the wearer's eye, with substantially no angular deviation in either the vertical or horizontal planes as illustrated by line 130 in FIGS. 9 and 10. Due to variations in the way a particular eyeglass will sit on the heads of different wearers, it may be convenient to reference a theoretical normal straight ahead line of sight which exhibits no vertical or horizontal deviation such as line of sight 27 or 130. Theoretical lines of sight can be standardized such as by reference to Alderson's head forms as will be understood by those of skill in the art.

The lens 14 is provided with an anterior surface 28, a posterior surface 30, and a varying thickness therebetween. The thickness of the lens 14 in the region of the medial edge 24 for a polycarbonate lens is generally within the range of from about 1 mm to about 2.5 mm, and preferably in the range of from about 1.5 mm to about 1.8 mm. In a preferred embodiment, the thickest portion of the lens 14 is at or about the intersection of the lens with the optical centerline, and is about 1.65 mm.

Preferably, the thickness of the lens 14 tapers smoothly, though not necessarily linearly, from the maximum thickness proximate the medial edge 24 to a relatively lesser thickness at the lateral edge 26. The thickness of the lens near the lateral edge 26 is generally within the range of from about 0.635 mm to about 1.52 mm, and, preferably, within the range of from about 0.762 mm to about 1.27 mm. In one preferred polycarbonate embodiment, the lens has a minimum thickness in the lateral zone of about 1.15 mm. The minimum thickness at lateral edge 26 is generally governed by the desired impact resistance of the lens.

Figure 3:
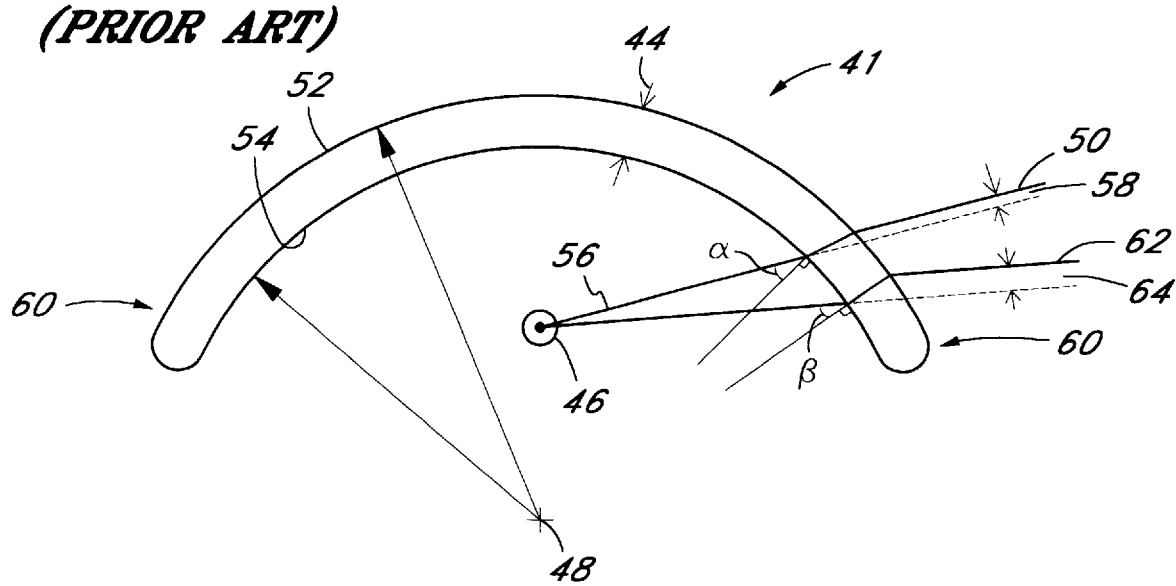
FIG. 3 is a schematic horizontal cross-sectional view of a prior art untapered lens for a dual lens eyewear system.

FIG. 3 schematically illustrates refraction in a prior art lens 41 with circular inside and outside surface horizontal cross-sections, having a uniform thickness 44. With such a lens 41, the angle of incidence of rays from the lens 41 to the eye 46 changes throughout the angular range of vision. For example, a ray which shall be referred to for descriptive purposes as a medial light ray 50 strikes the lens 41 at an angle α to the normal at the point of incidence. As is well known in this art, bending of light at transmitting surfaces depends in part upon the angle of incidence of light rays. The ray 50 is refracted or bent in opposite directions at each of an outer surface 52 and an inner surface 54 of the lens 41, resulting in a transmitted ray 56 parallel to the incident ray 50. The transmitted ray 50 is laterally displaced, relative to the path of the incident ray 50, by a distance 58. This displacement represents a first order source of (prismatic) optical distortion.

Furthermore, refractory displacement is even more pronounced at a lateral end 60 due to a greater angle of incidence β. A peripheral incident ray 62 experiences greater displacement 64 than the medial incident ray 50, in accordance with Snell's Law, as will be understood by those of ordinary skill in the optical arts. The discrepancy between the peripheral ray displacement 64 and the medial ray displacement 58 results in a second order of optical distortion. This second order of distortion may cause substantial warping of an image seen through relatively lateral portions of the lens 41.

Figure 4:
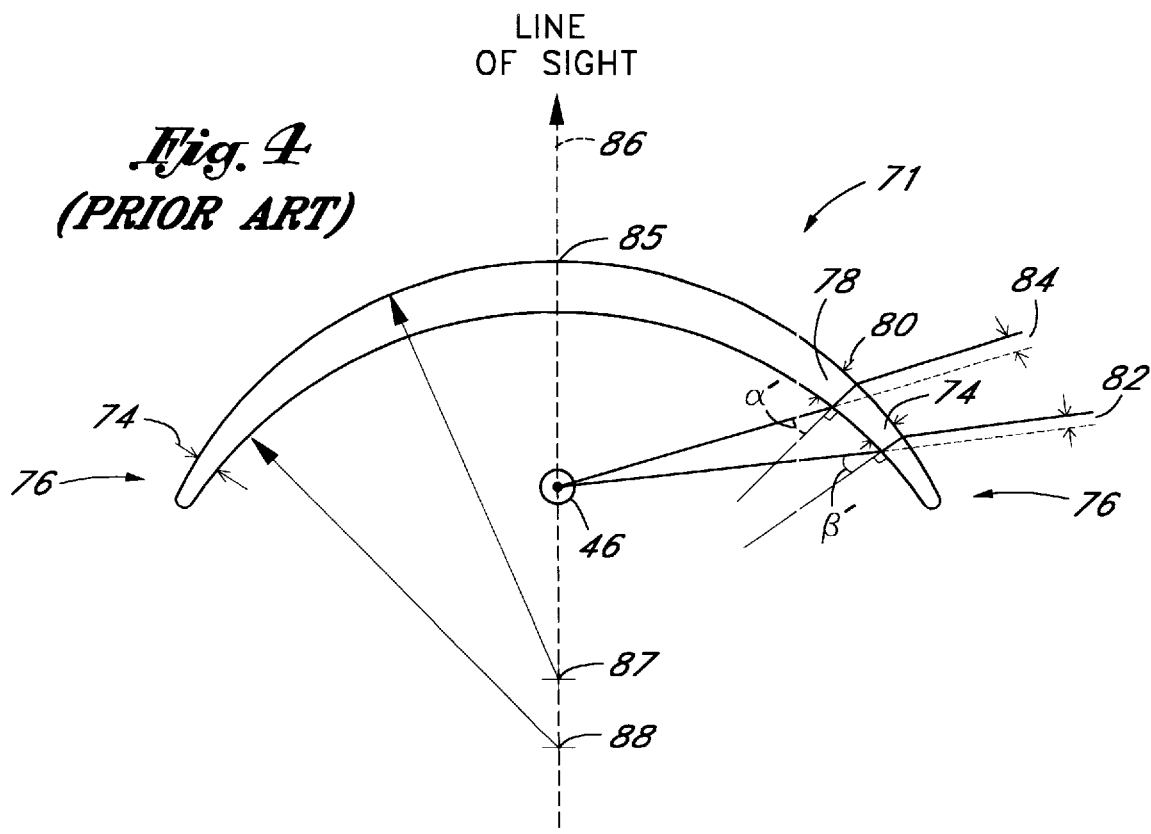
FIG. 4 is a schematic horizontal cross-sectional view of a tapered lens for a dual lens eyewear system.

FIG. 4 schematically illustrates a lens 71 of tapered thickness, to compensate for the greater angle of incidence at the lateral ends 60 of the lens 41 (FIG. 3), similar in ways to that disclosed in the context of unitary lens systems in U.S. Pat. No. 4,859,048, issued to Jannard. Tapering produces a smaller lens thickness 74 at a lateral end 76, relative to a lens thickness 78 at a more medial point 80. This smaller thickness 74 reduces an amount of peripheral ray displacement 82, relative to the peripheral ray displacement 64 through the untapered lens 41 of FIG. 4. In other words, lesser lens thickness 74 near the lateral end 76 of the tapered lens 71 compensates to some extent for a greater angle of incidence β', relative to the thickness 78 and angle of incidence α' at the more medial point 80.

The resulting difference between peripheral ray displacement 82 and medial ray displacement 84 on the same lens 71 is not as great as the corresponding difference in FIG. 3, reducing the second order optical distortion. Note that the degree of correction of the second order distortion depends upon a relationship between the manner and degree of tapering from the apex 85 to each lateral end 76 and the manner in which the angle of incidence changes over the same range.

The lens 71 of FIG. 4 is illustrated as though it were mounted within a frame (not shown) such that the wearer's normal line of sight 86 passes perpendicularly through the lens 71 at the lens apex or mechanical center 85. In other words, the angle of incidence to the lens normal is zero for the wearer's normal line of sight. The outer and inner surfaces of lens 71 in the cross-sectional illustration conform to offset, equal-radius circles represented by centerpoints 87 and 88, respectively. A line drawn through centerpoints 87 and 88, referred to herein as the optical centerline of the lens, is collinear with the normal line of sight in the as-worn orientation. This conventional configuration shall be defined as a centrally oriented lens, for ease of description. Circumferentially clockwise or counterclockwise of the normal line of sight 86, the angle of incidence to the lens normal increases in a regular fashion from zero at the lens apex 85.

A degree of wrap may be desirable for aesthetic styling reasons, for lateral protection of the eyes from flying debris, or for interception of peripheral light. Wrap may be attained by utilizing lenses of tight horizontal curvature (high base), such as small-radius spherical lenses, and/or by mounting each lens in a position which is canted laterally and rearwardly relative to centrally oriented dual lenses. Such canting shifts the normal line of sight 86 out of a collinear relationship with the optical centerline, and changes the optics of the lens. As a result, prior art dual lens eyewear with substantial "wrap" around the sides of a wearer's face has generally been accompanied by some degree of prismatic distortion.

Similarly, a high degree of rake or vertical tilting may be desirable for aesthetic reasons and for intercepting light, wind, dust or other debris from below the wearer's eyes. Just as wrap tends to shift the normal line of sight 86 out of a collinear relationship with a horizontal component of the optical centerline, mounting the lens with rake shifts the normal line of sight out of a collinear relationship with a vertical component of the optical centerline. Prior art dual lens eyewear with substantial rake generally also display a degree of prismatic distortion.

In accordance with the present invention, there is provided an improved optical configuration and method for minimizing prismatic distortion in a lens having rake and/or wrap in the as work orientation. Though the present invention may be applied to a wide variety of lens shapes and orientations, the invention has particular utility for dual lens eyewear using high base curvature and demonstrating a high degree of wrap and/or rake in the as-worn orientation.

Figure 5:
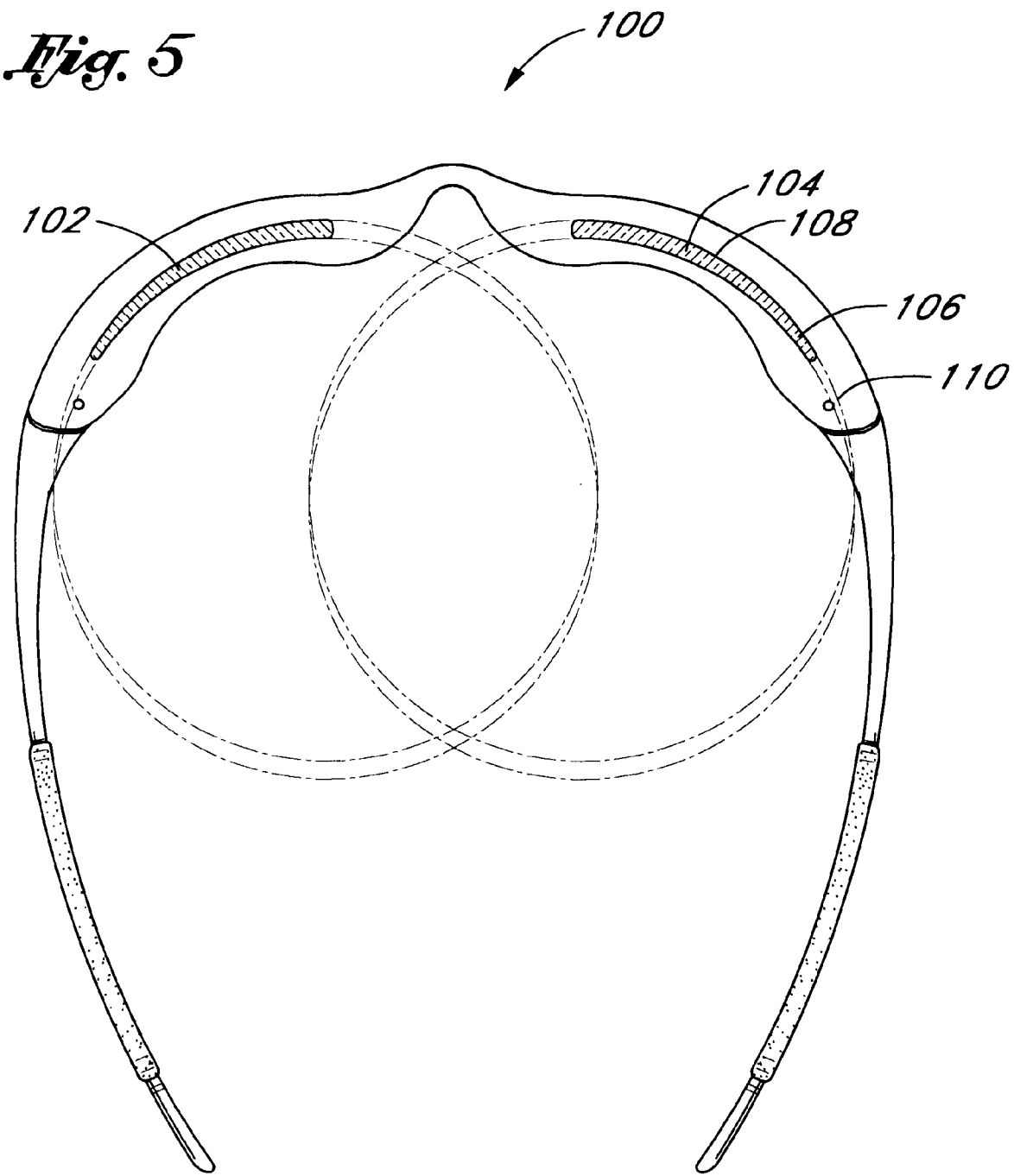
FIG. 5 is a cross-sectional view like that in FIG. 2, showing taper corrected lenses having a greater base curvature, in accordance with another embodiment of the present invention.

Referring to FIGS. 2 and 5, the illustrated eyewear incorporates canted lenses 12 and 14 or 102 and 104, mounted in a position rotated laterally relative to conventional centrally oriented dual lens mountings. A canted lens may be conceived as having an orientation, relative to the wearer's head, which would be achieved by starting with conventional dual lens eyewear having centrally oriented lenses and bending the frame inwardly at the temples to wrap around the side of the head.

As a consequence of the increased wrap, the wearer's normal line of sight 27 no longer strikes the lens 14 perpendicularly, as illustrated in FIG. 4. Instead, the angle of incidence θ° (FIG. 2) for the wearer's line of sight 27 is generally greater than 90°, and to achieve good wrap it may be greater than about 95°, preferably is within the range of from about 100° to about 135°, and in one 9.5 base embodiment is about 101.75°. Lower base lenses generally will exhibit a larger angle θ in the as worn orientation, and the angle θ in an embodiment having a base of 6.5 was about 113.4°. In a base 4 embodiment having a pupillary distance of 2.8 inches, the angle θ was about 119.864°.

FIG. 5 illustrates the horizontal cross-section of an eyeglass 100 in accordance with an embodiment of the present invention, similar in style to that illustrated in FIG. 2, except having lenses 102 and 104 of tighter curvature (higher base) as well as possibly greater wrap. When the eyeglass 100 is worn, a lateral edge 106 of the lens 104 wraps significantly around and comes in close proximity to the wearer's temple to provide significant lateral eye protection as has been discussed.

An anterior (front) surface 108 of the lens of the present invention will generally conform to a portion of the surface of a regular geometric solid, such as a sphere 110, shown here in horizontal cross-section. The front surfaces of spherical lenses 102 and 104 of the illustrated embodiment can, therefore, be characterized by a radius. By convention in the industry, the curvature may also be expressed in terms of a base value, such that the radius (R) in millimeters of the anterior surface of the lens is equal to 530 divided by the base curve, or $$R = \frac{530}{B} \quad (1)$$

The present invention provides the ability to construct dual lens eyeglass systems having relatively high wrap using lens blanks having a base curve of 6 or greater, preferably between about 7½ and 10½, more preferably between about 8 and 9½, and, in one embodiment between about 8¾ and 9. The radius of the circle conforming to the anterior surface of a base 8¾ lens, for example, is about 60.57 millimeters. For comparison, the radius of the circle which characterizes the anterior surface of a base 3 lens is about 176.66 millimeters.

The embodiment of the present invention illustrated in FIG. 5 may be cut from a base 8¾ lens blank having a thickness of about 0.0649 inches at the optical centerline and about 0.053 inches at reference a point two inches along the outer circumference of the lens from the optical centerline. Alternatively, the lens can be molded directly into its final shape and configuration.

Figure 6:
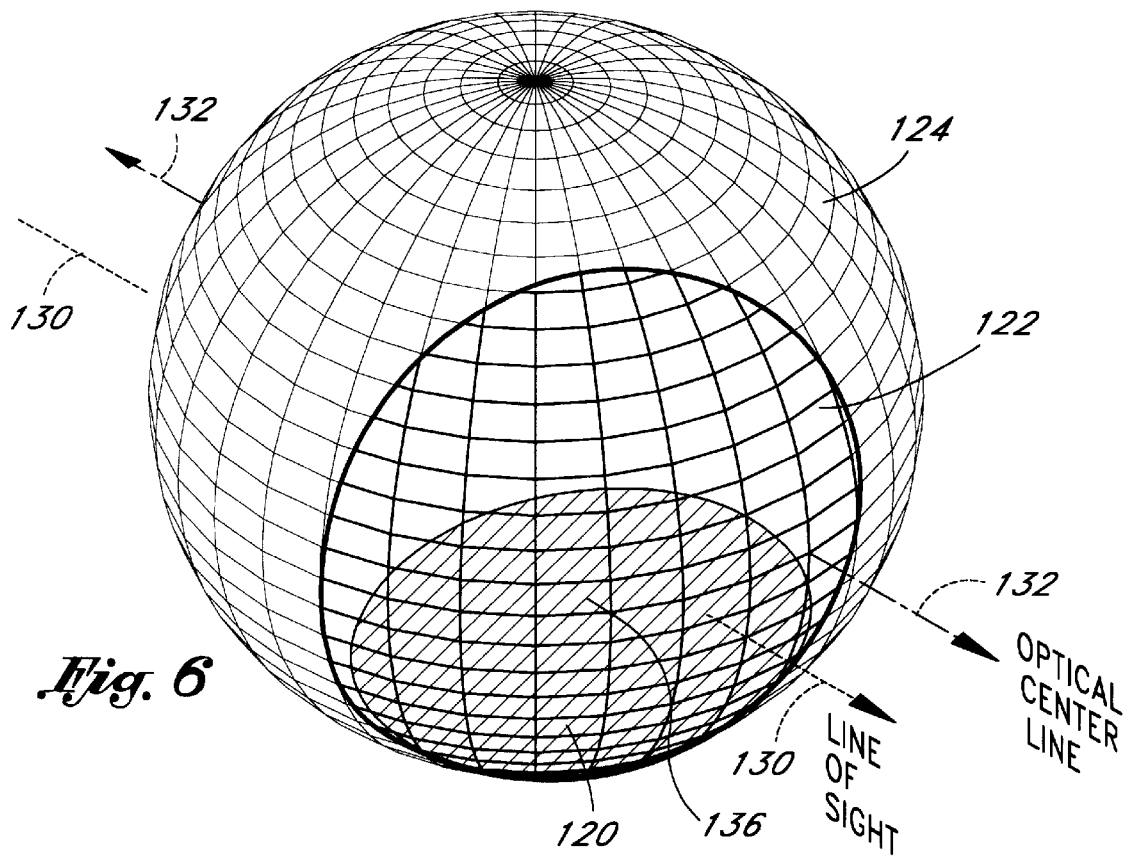
FIG. 6 is a perspective view of a lens blank conforming to a portion of the surface of a sphere, showing a lens profile to be cut from the blank in accordance with a preferred embodiment of the present invention.

FIG. 6 is a perspective view of a lens blank 122, a convex outside surface 136 of which generally conforms to a portion of the surface of a three-dimensional geometric shape 124. It will be understood by those of skill in this art that lenses in accordance with the present invention may conform to any of a variety of geometric shapes.

Preferably, the outside surface of the lens will conform to a shape having a smooth, continuous surface having a constant horizontal radius (sphere or cylinder) or progressive curve (ellipse, toroid or ovoid) or other aspheric shape in either the horizontal or vertical planes. The geometric shape 124 of the preferred embodiments herein described, however, generally approximates a sphere.

Figure 7:
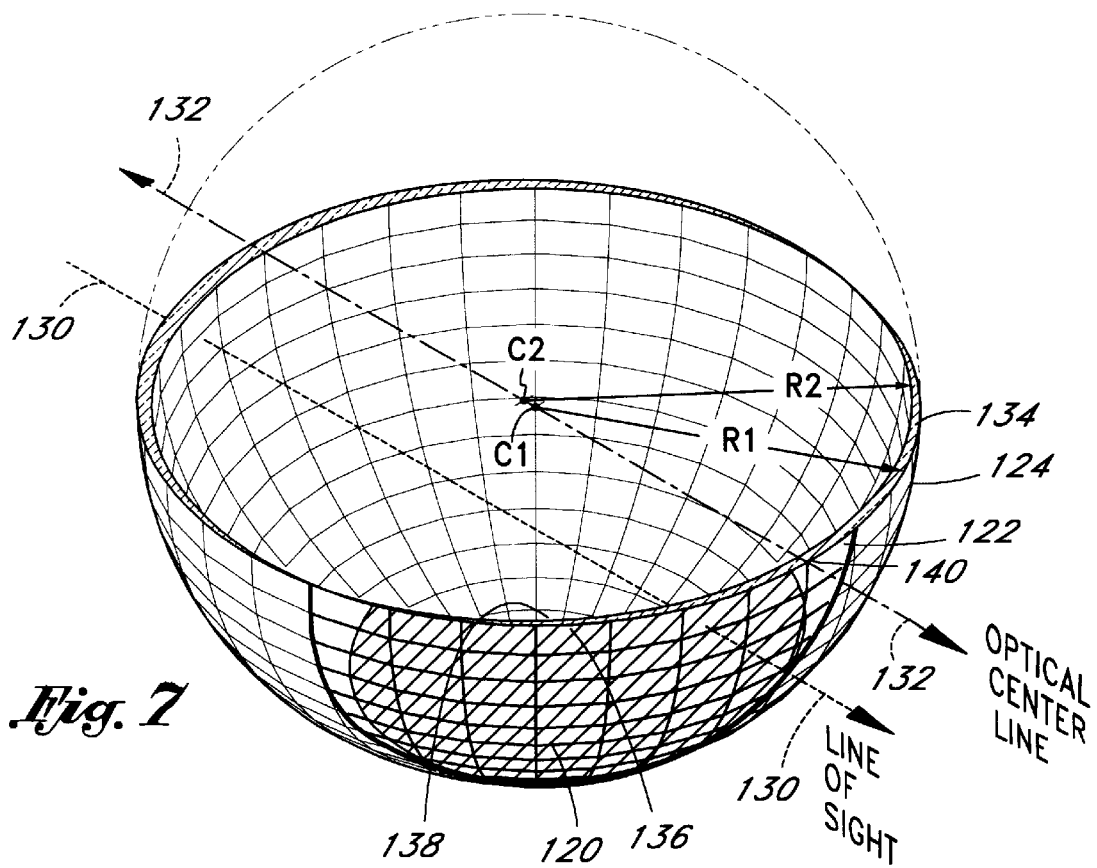
FIG. 7 is a perspective cutaway view of the hollow, tapered wall spherical shape, lens blank, and lens of FIG. 6.

The sphere 124 illustrated in FIGS. 6 and 7 is an imaginary three-dimensional solid walled structure, a portion of the wall of which is suitable from which to cut a lens 20. As is known in the art, precision lens cutting is often accomplished by producing a lens blank 122 from which a lens 120 is ultimately cut. However, it should be clear to those of skill in the art from the illustrations of FIGS. 6 and 7, that the use of a separate lens blank is optional, and the lens 120 may be molded directly into its final shape and configuration if desired.

It can also be seen from FIGS. 6 and 7 that the lens 120 and/or the lens blank 122 can be positioned at any of a variety of locations along the sphere 124. For the purpose of the present invention, the optical centerline 132 operates as a reference line for orientation of the lens 120 with respect to the sphere 124. In the illustrated embodiment, wherein both the outside surface and the inside surface conform to a portion of a sphere, the optical centerline is defined as the line 132 which joins the two centers C1 and C2. The analogous reference line for the purpose of nonspherical lens geometry may be formed in a manner different than connection of the two geometric centers of the spheres, as will be apparent to one of skill in the art.

The lens 120 is ultimately formed in such a manner that it retains the geometry of a portion of the wall of the sphere as illustrated in FIG. 7. The location of the lens 120 on the sphere 124 is selected such that when the lens 120 is oriented in the eyeglass frame, the normal line of sight 130 of the wearer through the lens will be maintained generally in parallel to the optical centerline 132 of the geometric configuration from which the lens 120 was obtained. In the illustration of FIGS. 6 and 7, the lens 120 is a right lens which has a significant degree of wrap, as well as some degree of downward rake (indicated by the as worn normal line of sight crossing the sphere 124 below the optical centerline 130). A lens having a different shape, or a lesser degree of wrap may overlap the optical centerline 132 of the imaginary sphere 124 from which the lens was formed. However, whether the optical centerline of the imaginary sphere 124 crosses through the lens 120 or not is unimportant, so long as the line of sight 130 in the lens 120 is maintained generally in parallel in the as-worn orientation with the optical centerline 132.

Similarly, if the lens is to have no rake or upward rake in the as worn orientation, the normal line of sight (and the entire lens) would cross the sphere 124 at or above the central horizontal meridian which contains the optical centerline. The spatial distance and position of the ultimate normal line of sight 130 relative to the optical centerline 132 therefore indicates the degree of wrap (by horizontal distance) and rake (by vertical distance). However, regardless of the distances involved, the lens will exhibit minimal optical distortion as long as the normal line of sight 130 is offset from but maintained substantially parallel to the optical centerline 132 preferably in both the horizontal and vertical planes.

For purposes of the present invention, "substantially parallel" shall mean that the preselected line of sight 130 when the lens 120 is oriented in the as worn position generally does not deviate within the horizontal or vertical plane by more than about ±15° from parallel to the optical centerline 132. Preferably, the normal line of sight 130 should not deviate by more than about ±10° from the optical centerline 132, more preferably the normal line of sight 130 deviates by no more than about ±5° and most preferably no more than about ±2° from parallel to the optical centerline 132. Optimally, the line of sight 130 is parallel to the optical centerline in the as worn orientation.

Variations from parallel in the horizontal plane generally have a greater negative impact on the optics than variations from parallel in the vertical plane. Accordingly, the solid angle between the line of sight 130 and optical centerline 132 in the vertical plane may exceed the ranges set forth above, for some eyewear, as long as the horizontal component of the angle of deviation is within the above-mentioned ranges of deviation from the parallel orientation. Preferably, the line of sight 130 deviates in the vertical plane no more than about ±10° and, more preferably, no more than about ±3° from the optical centerline in the as worn orientation.

FIG. 7 is a cutaway view of the lens 120, lens blank 122, and geometric shape 124 of FIG. 6. This view shows that the preferred geometric shape 124 is hollow with walls of varying thickness, as revealed by a horizontal cross-section 134 at the optical centerline of the geometric shape 124.

The tapered walls of the preferred geometric shape 124 result from two horizontally offset spheres, represented by their center points C1 and C2 and radii R1 and R2. An outer surface 136 of the preferred lens blank 122 conforms to one sphere (of radius R1) while an inner surface 138 of the lens blank 122 conforms to the other sphere (of radius R2). By adjusting the parameters which describe the two spheres, the nature of the taper of the lens blank 122 may also be adjusted.

In particular, the parameters for the two spheres to which the lens blank outer surface 136 and inner surface 138 conform is preferably chosen to produce minimal or zero refractive power, or non-prescription lenses. Where CT represents a chosen center thickness (maximum thickness of the wall of the hollow geometric shape 124), n is an index of refraction of the lens blank material, R1 is set by design choice for the curvature of the outer surface 136, R2 may be determined according to the following equation:

$$R_2 = R_1 - CT + \frac{CT}{n} \tag{2}$$

CT/n represents the separation of the spherical centers C1 and C2. For example, where a base 6 lens is desired as a matter of design choice, the center thickness is chosen to be 3 mm, and the index of refraction of the preferred material (polycarbonate) is 1.586, R2 may be determined as follows:

$$R_2 = \frac{530}{6} - 3 + \frac{3}{1.586} = 87.225 \text{mm} \tag{3}$$

For this example, the radius R1 of the outer surface 136 is equal to 88.333 mm, the radius R2 of the inner surface 138 is equal to 87.225 mm, and the spherical centers C1 and C2 are separated by 1.892 mm. These parameters describe the curvature of the lens blank 122 of a preferred decentered spherical embodiment.

In the case of the preferred embodiment, the optical centerline 132 is that line which passes through both center points C1 and C2 of the offset spheres. This happens to pass through the thickest portion of the preferred geometrical shape 124 walls at an optical center 140, though this may not be true for alternative nonspherical embodiments. The optical centerline 132 happens to pass through surface 136 of the illustrated lens blank 122, although this is not necessary. The optical center 140 does not happen to lie on the lens 120, although it may for larger lenses or lenses intended to exhibit less wrap in the as-worn orientation.

Figure 8:
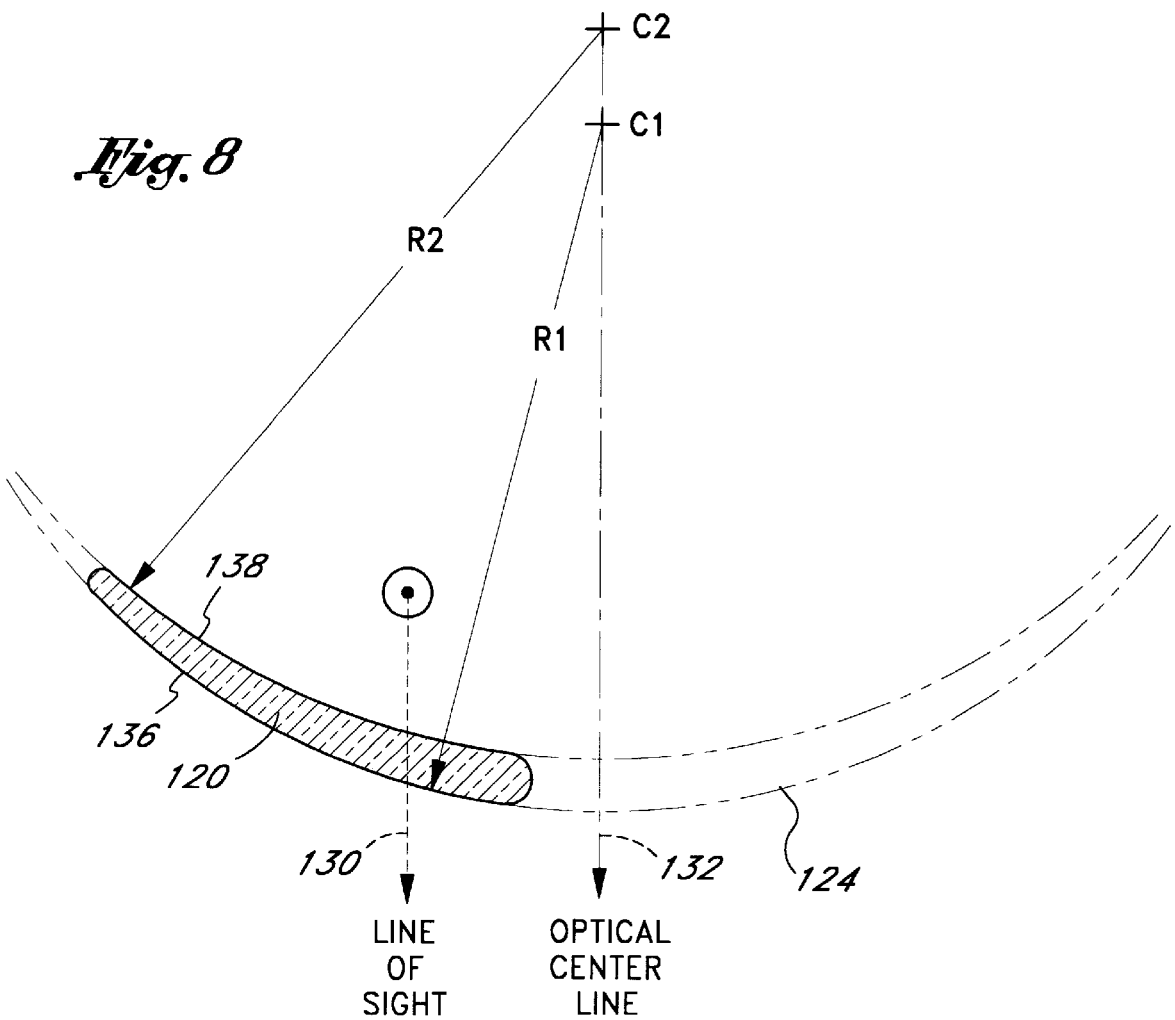
FIG. 8 is a horizontal cross-sectional view of a lens constructed in accordance with a preferred embodiment of the present invention.

FIG. 8 illustrates a horizontal cross-section of a lens 120, showing in phantom the geometric shape 124 to which the outer surface 136 and inner surface 138 conform. The lens blank 122 is omitted from this drawing. In accordance with the present invention, the optical centerline 132 associated with the chosen orientation is aligned to be generally parallel to but offset from the straight ahead normal line of sight 130 of the wearer as the lens 120 is to be mounted in an eyeglass frame.

Figure 8A:
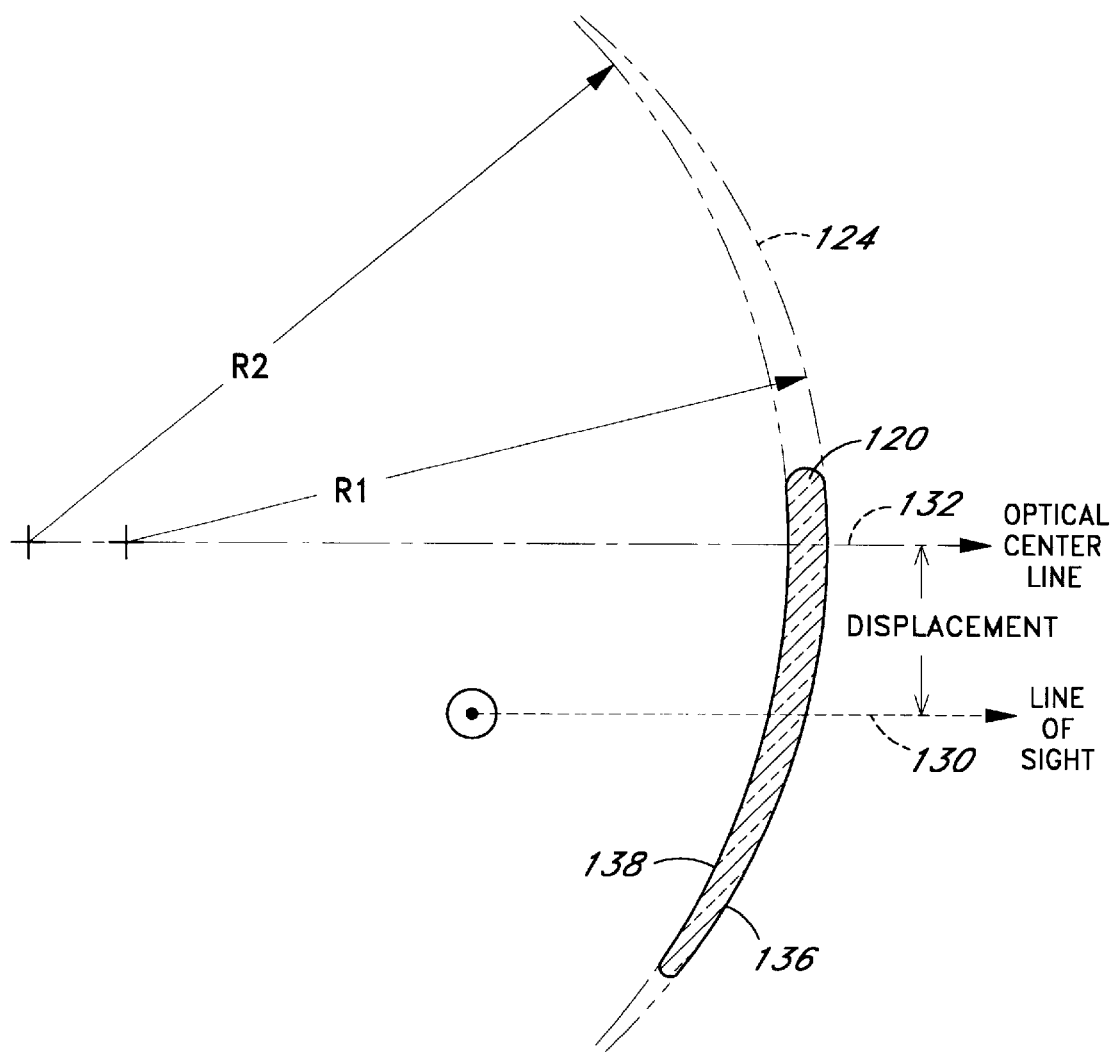
FIG. 8A is a vertical cross-sectional view of a lens constructed in accordance with a preferred embodiment of the present invention.

FIG. 8A illustrates a vertical cross-section of the lens 120, also showing in phantom the geometric shape 124 to which the outer surface 136 and inner surface 138 conform. Unlike the horizontal view of FIG. 8, the projection of the optical centerline 132 onto a vertical plane (i.e., the vertical component of the optical centerline 132) appears to pass through the vertical profile of the preferred lens 120. In any case, the vertical component of the optical centerline 132 associated with the chosen taper is also aligned to be generally parallel with the normal line of sight 130 of the wearer in the as worn orientation.

Thus, in addition to providing optically correct lenses for single or dual lens eyewear with a high degree of wrap, the present invention provides optically corrected lenses for eyewear characterized by upward or downward rake. The terms "rake" and "optically correct" are further defined below.

In general, "rake" will be understood to describe the condition of a lens, in the as worn orientation, for which the normal line of sight 130 (see FIG. 8A) strikes a tangent at the surface of the lens 120 at a non-perpendicular angle. For optically corrected eyewear in accordance with the preferred embodiment, however, the normal line of sight to a raked lens is generally parallel to and vertically offset from the optical centerline. Therefore, the degree of rake in a correctly oriented lens may be measured by the distance which the normal line of sight is vertically displaced up or down from the optical centerline.

Figure 10:
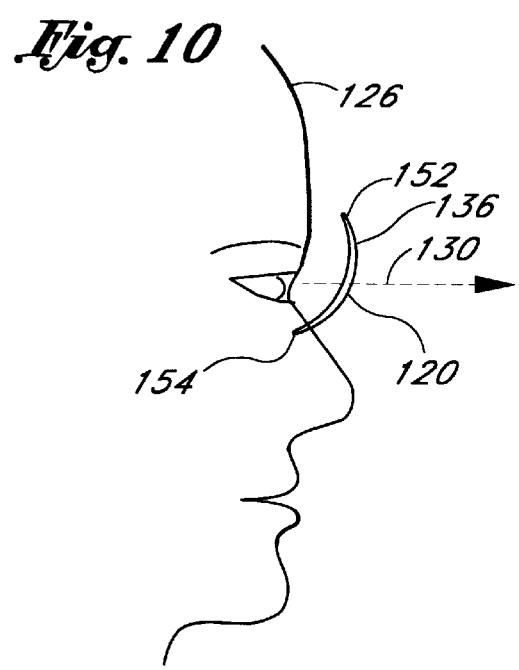
FIGS. 10A–10E are right side elevational views of lenses of various configurations and orientations relative to a wearer.
Figure 10C:
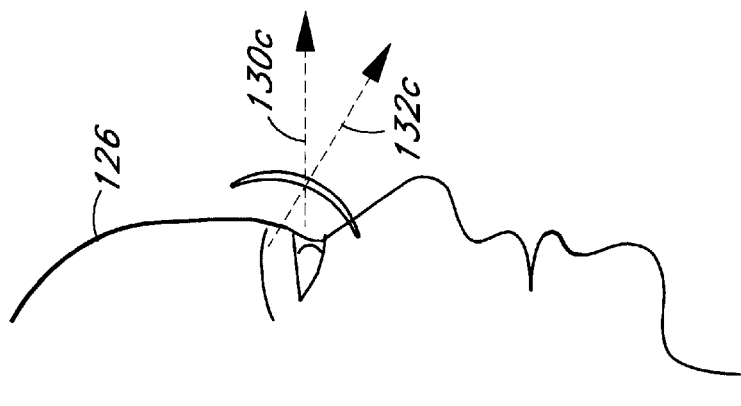
Figure 10B:
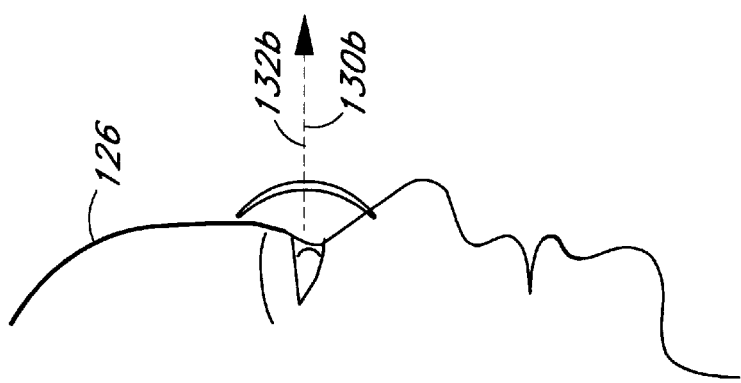

For a centrally oriented lens, as shown in FIG. 10B, the wearer's line of sight coincides with both the optical centerline and the mechanical centerline, thus displaying no vertical displacement. While such a lens may be optically corrected (as defined below) in the as worn orientation, the lens does not have rake, unlike the preferred embodiment of the present invention. FIG. 10C shows a lens orientation which is downwardly tilted or raked, but for which the optical centerline and the normal line of sight are highly divergent such that no "displacement" could meaningfully be measured. While such a lens may have downward rake in a conventional sense, advantageously providing downward protection for the eye and conforming to the wearer's face, it is not optically corrected in the as worn orientation for the straight ahead line of sight.

In contrast, the normal line of sight through a raked lens, made in accordance with the preferred embodiment, is characterized by a finite vertical displacement from the optical centerline, preferably a downward displacement for downward rake. Where the optical centerline diverges from the normal line of sight within the acceptable angular ranges set forth above, this displacement should be measured at or near the lens surface. The displacement may range from about any non-zero displacement to about 8.0 inches. Lenses of lower base curvature may require a greater displacement in order to achieve good rake. The vertical displacement for a lens of base 6 curvature, however, should be between about 0.1 inch and about 2.0 inches. More preferably, the vertical displacement is between about 0.1 inch and about 1.0 inch, particularly between about 0.25 inch and about 0.75 inch, and most preferably about 0.5 inch.

"Optically correct," as that term has been used in the present description, refers to a lens which demonstrates relatively low distortion in the preselected (e.g. straight ahead) line of sight as measured by one or more of the following values: prismatic distortion, refractive power and astigmatism. Raked lenses in accordance with the preferred embodiment demonstrate less than about $1/8$ diopters prismatic distortion, preferably less than about $1/16$ diopters, and more preferably less than about $1/32$ diopters. Refractive power and astigmatism for lenses in accordance with the present invention are also preferably low. Each of refractive power and astigmatism are preferably less than about $1/8$ diopters, more preferably less than about $1/16$ diopters and most preferably less than about $1/32$ diopters.

It will be understood by the skilled artisan that the advantages in minimizing optical distortion apply to both the horizontal and the vertical dimensions. Particular advantage is derived by applying the principles taught herein to both vertical and horizontal dimensions of the lens, enabling the combination of lateral and lower peripheral protection of the eyes (through wrap and rake) with excellent optical quality over the wearer's full angular range of vision.

Furthermore, although the principal embodiments described herein are of constant radius in both the horizontal and vertical cross-section, a variety of lens configurations in both planes are possible in conjunction with the present invention. Thus, for example, either the outer or the inner or both surfaces of the lens of the present invention may generally conform to a spherical shape as shown in FIGS. 6 and 7. Alternatively either the outer or the inner or both surfaces of the lens may conform to a right circular cylinder, a frusto-conical, an elliptic cylinder, an ellipsoid, an ellipsoid of revolution, toroid, other asphere or any of a number of other three dimensional shapes. Regardless of the particular vertical or horizontal curvature of one surface, however, the other surface should be chosen such as to minimize one or more of power, prism and astigmatism to produce an optically correct lens in the mounted and as worn orientation.

FIGS. 9–12 will aid in describing a method of choosing a location on the lens blank 122 from which to cut the right lens 120, in accordance with a preferred dual lens eyeglass embodiment of the present invention. It will be understood that a similar method would be used to construct the left lens for the dual lens eyewear of the preferred embodiment.

As a first step, a desired general curvature of the lens inner or outer surface 138, 136 may be chosen. For the preferred lens 120, this choice determines the base value of the lens blank 122. As noted elsewhere herein, a number of other curvatures may be utilized in conjunction with the present invention. A choice of lens thickness may also be preselected. In particular, the minimum thickness may be selected such that the lens will withstand a preselected impact force.

Figure 12:
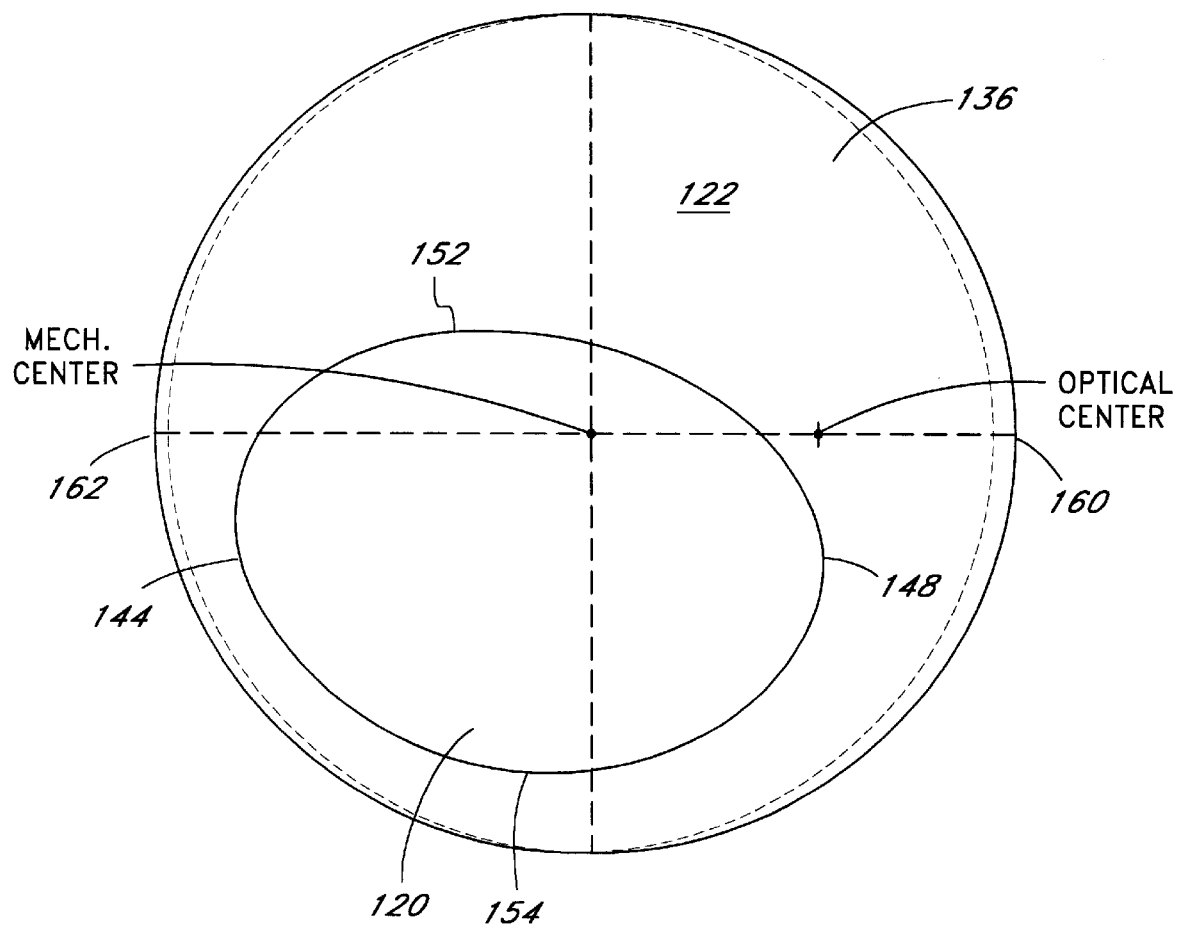
FIG. 12 is a top plan view of the right lens and front (convex surface) of the lens blank of FIG. 6, rotated to project the mechanical centerline of the blank normal to the page.

A desired lens shape may also be chosen. For example, FIG. 12 illustrates an example of a front elevational shape for the lens 120. The particular shape chosen is generally not relevant to the oriented decentered lens optics disclosed herein.

Figure 9:
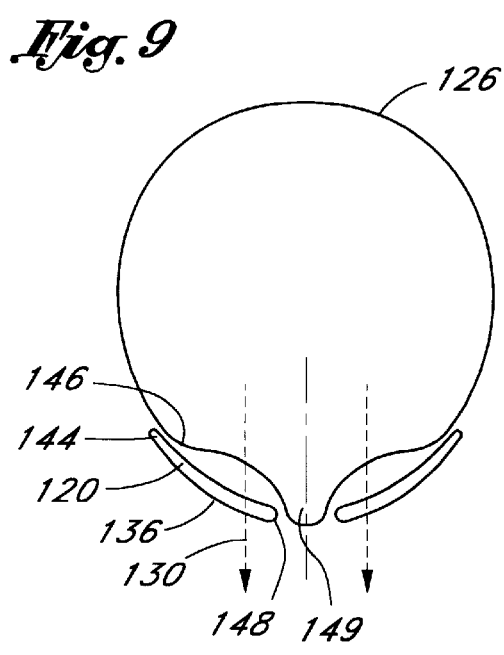
FIG. 9 is a top plan view of the lens of FIG. 8 showing a high wrap in relation to a wearer.

A desired as-worn orientation for the lens should also be chosen, relative to the normal line of sight 130 of the wearer 126. As mentioned above, preferred orientations may provide significant lateral wrap for lateral protection and interception of peripheral light, and for aesthetic reasons. For example, the embodiment illustrated in FIGS. 6–12 uses a canted lens 120 to achieve wrap. Alternatively, wrap may be achieved through use of a higher base lens and a more conventional (non-canted) orientation. FIGS. 9 and 10 illustrate more plainly how the orientations may be related to the line of sight 130 of the wearer.

Figure 10A:
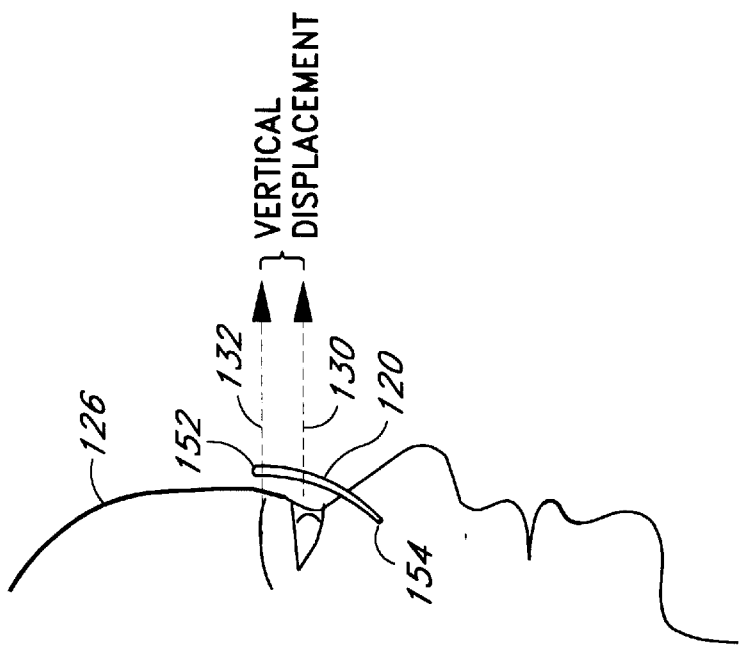
Figure 10E:
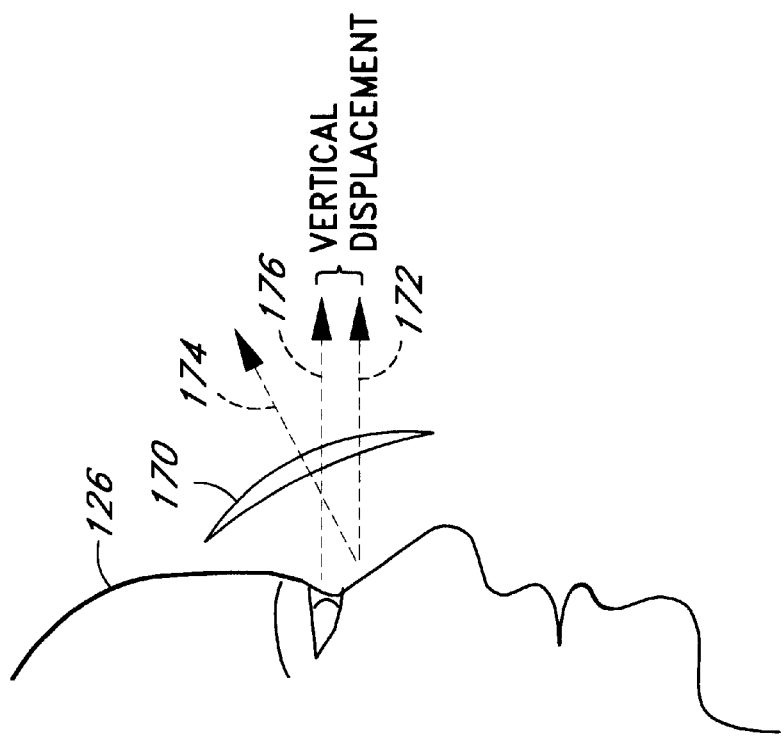

The eyewear designer may also choose a degree of rake, or vertical tilt, as will be understood from FIGS. 10A–10E, schematically illustrating various vertical as worn orientations of a lens, relative to the head of the wearer 126. FIG. 10A illustrates a preferred orientation of a dual lens 120 relative to the head of the wearer 126, and relative in particular to the straight ahead normal line of sight 130. A downward rake, as illustrated in FIG. 10A, is desirable for certain eyeglass systems for a variety of reasons, including improved conformity to common head anatomy. Some degree of upward rake may be desirable, for example, in certain football or other helmet shields or protective goggles. See, e.e., FIG. 10E and discussion, infra.

As will be apparent to those of skill in the art in view of the disclosure herein, a lens 120 having a mechanical center point which falls below the horizontal plane intersecting the optical centerline 132 (see FIG. 7) will permit the lens to be oriented with a downward rake as illustrated in FIG. 10 and yet preserve a generally parallel relationship between the optical centerline and the straight ahead line of sight to produce an optically correct lens in the properly as worn orientation. Since the orientation of the lens 120 to the optical centerline 122 in the imaginary sphere should be the same as the orientation between the lens 120 and a parallel to the normal line of sight 130 in the as-worn orientation, any lens cut from this sphere below the optical centerline 132 can be mounted with a corresponding degree of downward rake and achieve the optical correction of the present invention. Lenses centered above the optical centerline 132 can be optically corrected in an as worn orientation with a commensurate degree of upward rake.

Accordingly, the desired degree of rake may be chosen by specifying a vertical component of the displacement between the normal line of sight 130 and the optical centerline 132, as illustrated in FIG. 10A. Either way, the greater the displacement, the greater the rake. In general, the vertical displacement in accordance with the present invention will be greater than zero. Generally it will be from about 0.1 inches to about 2 inches in dual lens eyeglasses depending upon base curvature. Preferably, vertical displacement will be from about 0.1 inches to about one inch, or about 0.2 inches or greater. More preferably, it will be from about 0.25 inches to about 0.75 inches and in one embodiment it was about 0.5 inches.

Alternatively, a general profile may be chosen which fixes an orientation of the normal line of sight relative to the curvature of the lens (not accounting for the thickness of the lens). For instance, both FIG. 10A provides reference points of a top edge 152 and a bottom edge 154 relative to the normal line of sight 130. This relationship may then be utilized to determine the position on a lens blank from which to cut the lens, as will be clear from the discussion of FIG. 11A below.

Figure 11:
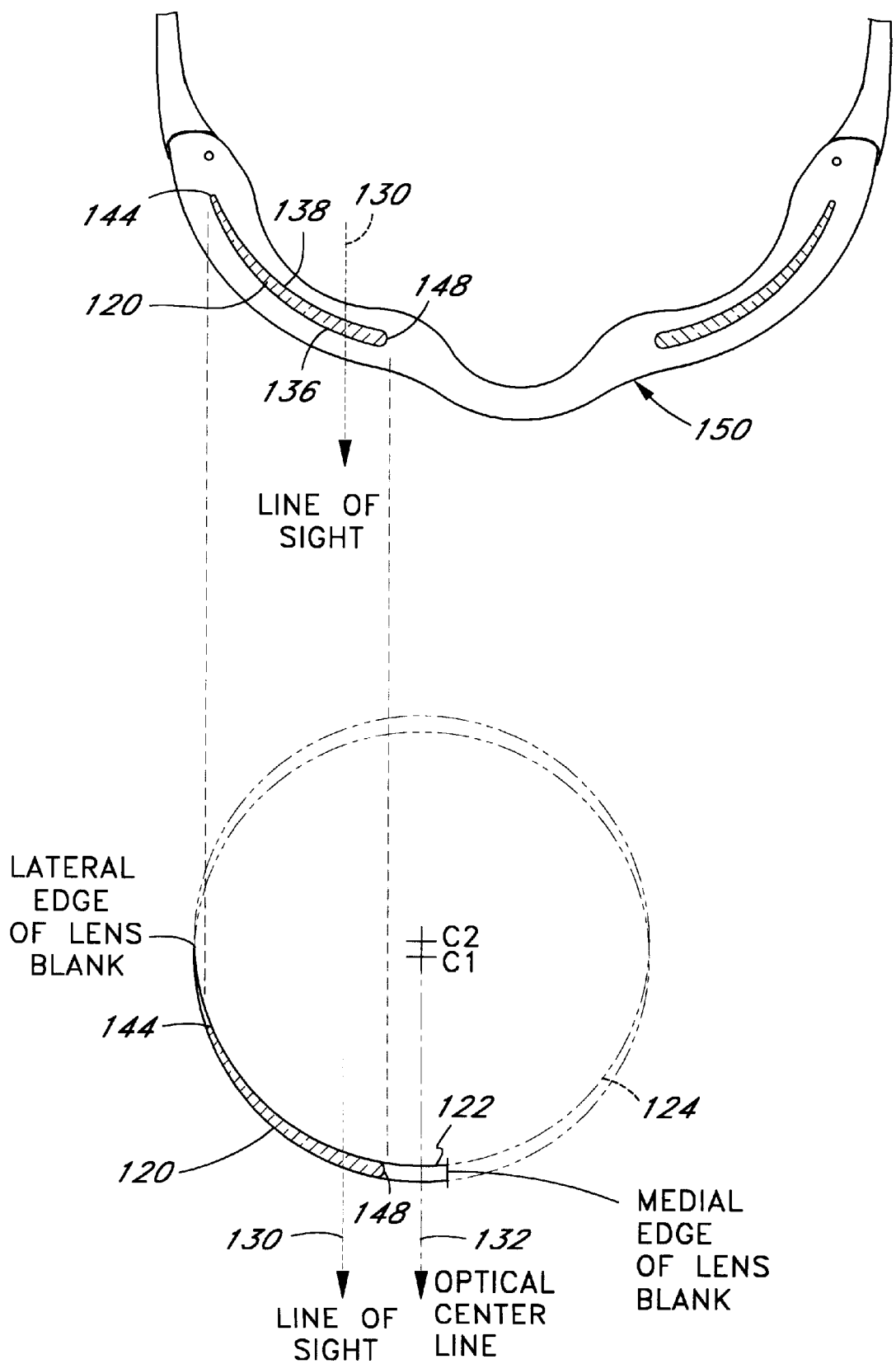
FIG. 11 schematically illustrates the projection of the lens horizontal profile from a desired orientation within an eyewear frame to the lens blank, in accordance with a preferred embodiment of the present invention.

Referring now to FIG. 11, a mapping of the horizontal orientation of the lens 120 onto the lens blank 122 is illustrated. The normal line of sight 130, with respect to which the chosen orientation is measured, is maintained substantially parallel to and offset from the optical centerline 132. The horizontal component of the displacement will generally be within the range of from about 0.1 inches to about 8 inches for lower base curvatures.

Once the aesthetic design and desired rake and wrap orientation such as that illustrated in FIG. 11 has been determined (such as by the chosen frame 150), and the lens blank 122 formed having a suitable base curvature for fitting within the aesthetic design, the aesthetic design may be "projected" graphically or mathematically onto the surface of the theoretical sphere or blank to reveal that portion of the sphere which is suitable for use as the lens 120. The projection of the lens shape onto the sphere should be moved about the surface of the sphere until it is positioned such that the lens cut from the sphere at that location will exhibit the appropriate wrap and rake for the aesthetic design without any rotation of the lens 120 out of its orientation in which the optical centerline of the sphere is generally parallel to the desired normal line of sight in the as-worn orientation.

Figure 11A:
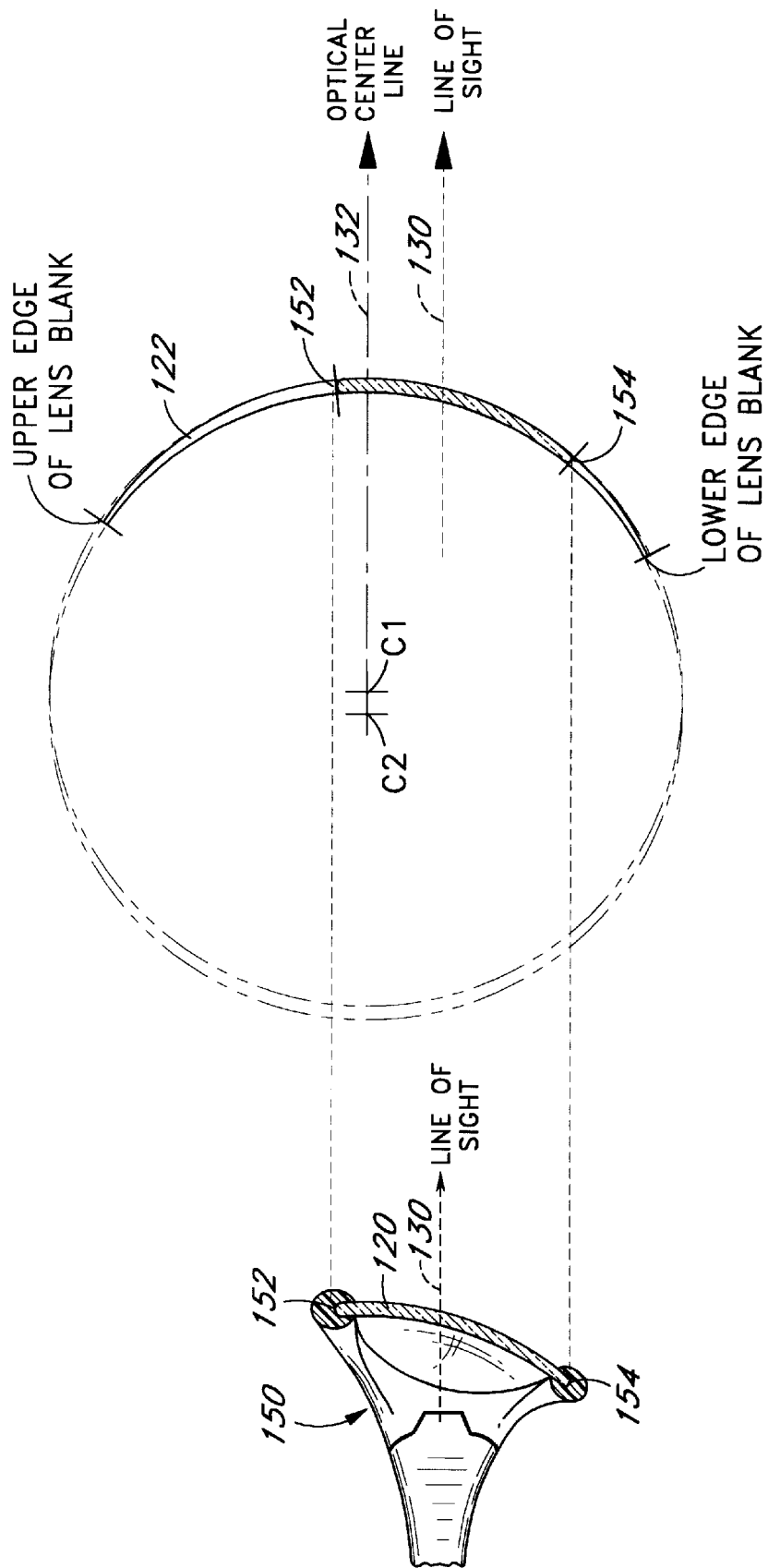
FIG. 11A schematically illustrates the projection of the lens vertical profile from a desired orientation within an eyewear frame to the lens blank, in accordance with a preferred embodiment of the present invention.

A similar simultaneous projection may be performed for the vertical orientation chosen, as depicted in FIG. 11A. FIG. 11A schematically represents the projection from the chosen frame 150 to a position on the lens blank 122. The frame 150 (or a conceptual configuration such as provided by FIG. 10A) provides reference points in the form of the lens top edge 152 and bottom edge 154 in relation to the line of sight 130. The projection may then be shifted up or down until the top edge 152 and the bottom edge 154 are both simultaneously aligned with corresponding points on the outer surface 136 of the lens blank, while maintaining the line of sight 130 substantially parallel with the optical centerline 132.

Projection of both the horizontal profile and the vertical profile may be performed simultaneously, locating a unique position on the lens blank 122 corresponding to the desired three-dimensional shape of the lens (including the front elevational shape shown in FIG. 12) at which the line of sight 130 is parallel to the optical centerline 132 or other reference line of the lens blank 122. Of course, it will be understood that the lines 130 and 132 may be substantially parallel, that is, within the acceptable range of angular deviation set forth above.

This shape may then be cut from the blank 122 or molded directly in the final lens configuration. The resultant lens 120 not only conforms to the desired shape, but also minimizes prismatic distortion when in the as worn orientation.

FIG. 12 illustrates a lens blank 122, concave towards the page such as that shown conforming to a portion of the surface of the sphere in FIGS. 6 and 7. In FIG. 12, the lens blank 122 has been formed on the theoretical sphere such that the mechanical center of the blank is illustrated in the center of the drawing on the central horizontal meridian. The illustrated lens profile 120 has a medial edge 148, a lateral edge 144, an upper edge 152 and a lower edge 154. The medial edge 148 of the right lens 120 lies close to the optical center of the lens blank 122.

At least a portion of the right lens 120 lies in the lower left-hand (third) quadrant of the lens blank 122. Preferably, in an embodiment of the invention exhibiting both wrap and downward rake, at least about half of the lens area will fall within the third quadrant of the lens blank 122. Preferably all or substantially all of the area of the lens 120 will lie below and to the left of the optical center as illustrated. Lenses exhibiting a similar degree of rake but lesser wrap may be positioned on the lens blank 122 such that as much as 50% or more of the lens area is within the lower right (second) quadrant of the lens blank 122.

FIG. 12A illustrates the position on the same lens blank 122 from which a left lens 120L could be cut. The left lens 120L has a medial edge 148L, a lateral edge 144L, an upper edge 152L and a lower edge 154L. The left lens 120L is drawn in phantom because both the right lens 120 and the left lens 120L for the illustrated profile cannot be cut from the same lens blank 122. Rather, the illustrated left lens 120L would be cut from the position shown on a second lens blank which is identical to the first lens blank 122.

As the left lens 120L should be symmetrically opposite to the right lens 120, the left lens 120L is a mirror image of the right lens 120. For example, the image of the right lens 120 may be flipped across a vertical plane through which the optical centerline 130 and poles of the sphere 124 pass. The lens blank upon which that image would be projected may be identical to the illustrated lens blank 122, but rotated 180° about the mechanical center.

Alternatively, the left lens 120L position may also be considered the mirror image of the right lens 120 across an axis of vertical symmetry. As illustrated in FIG. 12B, the left lens 120L is upsidedown relative to the right lens 120. For the preferred lens blank 122, the axis of vertical symmetry is a central horizontal meridian 170 which divides the lens blank 122 into upper and lower halves, each of which conform to upper and lower hemispheres of the sphere 124 (FIGS. 6 and 7). Thus, the horizontal position (i.e., distance from the medial or lateral edge of the lens blank 122) for each of the medial edge 148L, lateral edge 144L, upper edge 152L and lower edge 154L, is the same for corresponding points of the right lens 120. Corresponding points on the left and right lenses are also the same vertical distance from the horizontal meridian 170, but in the opposite directions. For example, the upper edge 152L of the left lens 120L is about the same distance above the horizontal meridian 170 as the upper edge 152 of the right lens 120 is below the horizontal meridian 170.

Thus, the left lens 120L of any raked dual lens embodiment is cut substantially from the upper half of preferred lens blank 122, while the right lens 120 is cut substantially from the lower half of an identical lens blank. Preferably, where a dual lens embodiment displays both wrap and rake, the left lens 120L is cut substantially from the upper left (fourth) quadrant of the preferred lens blank 122, while the right lens is cut substantially from the third quadrant. "Substantially," as used in this context, refers to more than 50% of the surface area of the lens 120 or 120L falling within the relevant half or quadrant of the preferred lens blank 122.

Of course, this description is limited to a lens blank 122, which is described by an optical centerline passing through the central horizontal meridian 170 (i.e., the lens blank 122 taper is vertically symmetrical) but not through the mechanical center (i.e., the lens blank 122 taper is horizontally asymmetrical). It will be understood that alternative lens blanks may utilize alternative tapering. The skilled artisan may adjust the positions from which to cut the right and left lenses such that the normal line of sight in the as worn orientation is maintained substantially parallel to the optical centerline, regardless of the tapering symmetry.

The present invention thus provides a precise method of furnishing the correct correspondence between taper and the varying angle of incidence from the wearer's eye to the surface of a lens. By recognizing a novel relationship among the wearer's line of sight and the form of taper, the present invention allows use of any of a variety of lens designs while minimizing astigmatism, power and prismatic distortion. For example, a designer may choose a desirable orientation and curvature for the lens, relative to a wearer's line of sight. The orientation and curvature may be chosen from a wide range of rake, wrap, base value and proximity to a wearer's face. The form of taper and location of the lens profile on the theoretical sphere or other shape may then be chosen, by the method of the present invention, such that the prismatic distortion in the as worn orientation is minimized.

Figure 13:
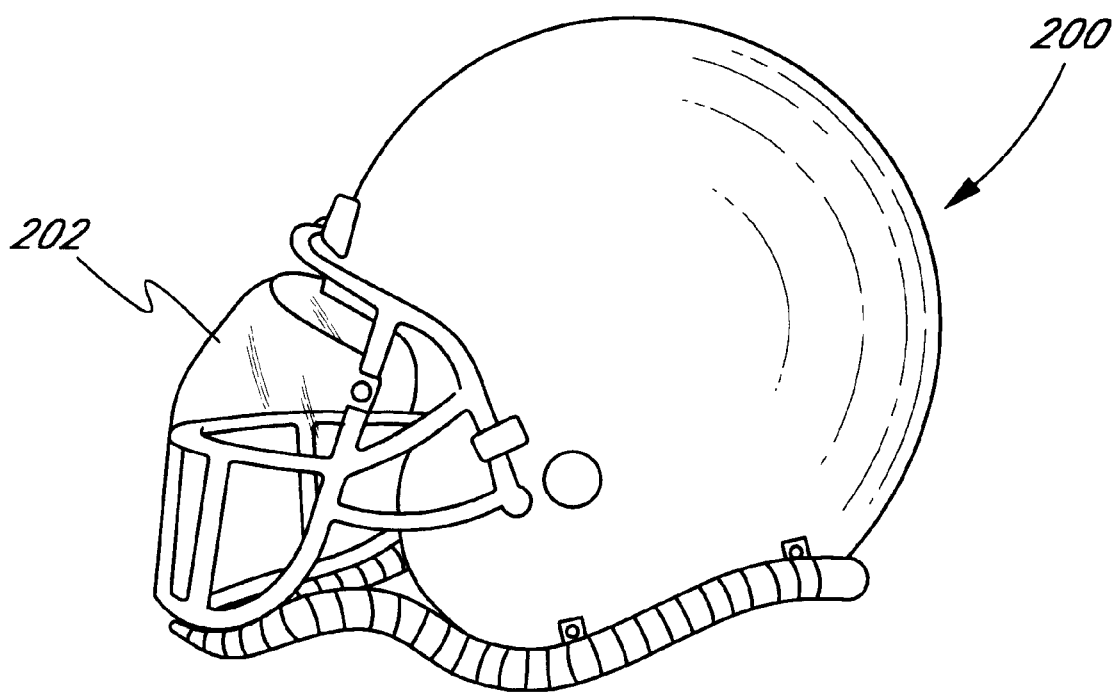
FIG. 13 is a right side elevational view of a safety helmet in accordance with a preferred embodiment of the present invention.

In accordance with a further aspect of the present invention, the foregoing principles can readily be applied to unitary lens eyeglass systems as well as protective eye shields such as may be incorporated into sport safety helmets and goggles. FIG. 13 shows an exemplary sport safety helmet 200, incorporating a safety shield 202. Such helmets are useful in a variety of activities such as motorcycle and other motor vehicle riding, football, lacrosse, ice hockey and the like. See, for example, U.S. Pat. No. 4,633,531 to Nimmons entitled "Tension Mounting for Face Guard," the disclosure of which is incorporated herein by reference. The helmet 200 of FIG. 13 is particularly adapted to football applications. Corrected, oriented unitary shields of the present invention may also be readily incorporated into such eyewear as motorcycle goggles, ski goggles, and the like. See, for example, U.S. Pat. No. 4,447,914 to Jannard entitled "Goggle", the disclosure of which is incorporated herein by reference. Masks for underwater diving and a variety of industrial safety applications may also utilize the lens of the present invention. In addition, the oriented corrected unitary lens of the present invention is highly useful in unitary lens eyeglasses such as those disclosed in U.S. Pat. No. 4,824,233 to Jannard, entitled "Multi-Component Sunglasses;" U.S. Pat. No. 4,867,550 to Jannard, entitled "Toroidal Lens for Sunglasses;" and U.S. Pat. No. 5,208,614 to Jannard entitled "Concavely Indented Lenses for Eyewear," the disclosure of each of which is hereby incorporated by reference herein.

In general, for the purpose of such applications as a football helmet, the horizontal arc length of the shield will be within the range of from about 6" to about 14". In most applications, the arc length along the central horizontal meridian will be within the range of from about 8" to about 12". In one particular football helmet application, the arc length along the central horizontal meridian was about 10".

The arc length along the surface of the shield in the vertical direction will generally be in the range of from about 2" to about 6". Preferably, the arc length in the vertical direction will be within the range of from about 2½" to about 5", and, in one particular football helmet embodiment, the vertical arc length of the shield was about 3.5". The arc length of the shield in either the horizontal or the vertical directions may vary at different points in the shield, such as due to cutouts, attachment structures, and other features useful for adapting the shield to fit within the helmet or other support structure.

In one football helmet embodiment of the shield of the present invention, the thickness of the shield at its optical centerline was about 0.125". The thickness of the shield along the bottom edge was in the area of from about 0.120" to about 0.123", such as about 0.121". The thickness of the shield along the lateral edges was roughly the same as the thickness at the bottom. Thus, the shield was provided with a taper from a relatively thick point within the body of the shield, to relatively thinner portions around the peripheral edges of the shield.

The preferred lens (shield) geometry may be either spherical or toroidal. In particular, at least the front surface of the shield conforms either to a portion of the surface of a sphere or a portion of the surface of a toroid. Other lens geometries such as elliptical or aspheric may also be utilized, and the optics may be optimized in accordance with the principles disclosed herein.

For example, in one football helmet embodiment of the shield of the present invention, the shield conformed to a portion of the surface of a toroid having a first radius in the horizontal direction and a second radius in the vertical direction. By definition, if the horizontal and vertical radii on the same lens surface are equal, that lens surface has spherical geometry. In the preferred toroidal geometry shield, the horizontal curvature is within the range of from about 3 base to about 6 base. The vertical curvature is different than the horizontal curvature, and is within the range of from about 2 base to about 4 base. In one particular football helmet embodiment, the shield has toroidal geometry with a horizontal 5 base and a vertical 3 base curvature.

Figure 10D:
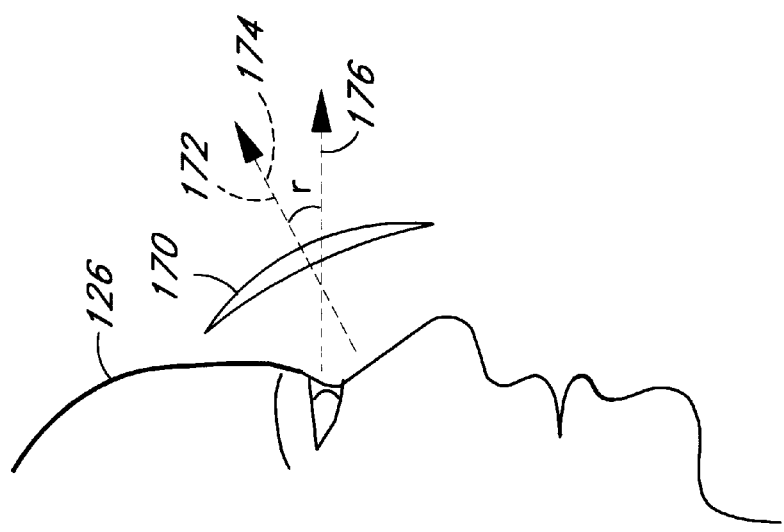

Shields for football helmets which have toroidal or spherical geometry and a taper towards the peripheral edges are known. See, for example, FIG. 10D. However, the shields 170 in the prior art are mounted in such a manner that the optical centerline 172 of the shield 170 is coincident with the mechanical centerline 174 of the shield 170. As mounted in many football helmets, goggles, and other support structures such as described above, the mechanical centerline 174 is often not coincident with the wearer's straight-ahead normal line of sight 176. In particular, in the case of a football helmet, the protective shield 170 is often raked in an upward direction as illustrated in FIG. 10D. In other words, the mechanical centerline 174 of the shield 170 is angled upwardly in a forward direction from the wearer with respect to the wearer's straight-ahead normal line of sight 176 by an angle r. As a consequence, in accordance with the principles previously disclosed herein, at least prismatic distortion is introduced with respect to the wearer's straight-ahead normal line of sight.

Thus, in accordance with the present invention, the shield 170 is cut from the blank or molded such that, in the vertical plane, the optical centerline 172 of the shield is rotated away from the mechanical centerline 174. For a shield which is to be mounted with upward rake, the optical centerline will also be displaced downwardly from the normal line of sight 176. See FIG. 10E, in which the illustrated lens curvature is schematic only. Refer for comparison to FIG. 11a, which illustrates correction in the vertical plane for an eyeglass having downward rake. The shield 170 of the present invention which is corrected for upward rake must be conceptually cut from a position on the blank 122 which is shifted higher along the lens blank 122 compared to the lens illustrated in FIG. 11a.

Once the lens is properly cut or molded, it must then be oriented in the support structure such that it retains a parallel or substantially parallel relationship between the wearer's preselected reference line of sight and the optical centerline 172 of the shield. For most applications, the wearer's preselected reference line of sight will be the wearer's straight-ahead normal line of sight 176. Thus, referring to the vertical plane orientation illustrated in FIG. 10E, the protective shield 170 of the present invention is configured such that the optical centerline 172 of the shield 170 is spaced apart from but generally parallel to the wearer's straight-ahead normal line of sight 176 in the as-worn orientation. The ideal orientation of the shield in a football helmet or other support structure also maintains the horizontal view optical centerline of the shield (not illustrated) generally parallel to the wearer's straight-ahead normal line of sight. As with previous embodiments, the properly tapered and oriented shield will be optically corrected if at least one and preferably two or all three of prism, power and astigmatism are less than about 1/8 diopters, more preferably less than about 1/16 diopters and optimally less than about 1/32 diopters.

Viewed from a different perspective, the shield of the present invention can be characterized by an optical centerline as has been disclosed previously herein, and a mechanical centerline. The mechanical centerline is a line that extends through the shield at a point lying halfway between the left side and the right side of the shield and also halfway between the top edge and the bottom edge of the shield. The mechanical centerline extends through the shield at that point at a perpendicular to a tangent to the surface of the shield at that point.

Lenses or shields produced in accordance with the present invention are thus provided with an angular deviation between the optical centerline 172 and the mechanical centerline 174 in the vertical plane. The degree of angular deviation between the optical centerline and the mechanical centerline in the vertical plane will depend upon the degree of rake with which the shield is ultimately mounted in the as-worn orientation to achieve optical correction. Generally the angle will be more than about 2° or 3°, and typically will be within the range of from about 5° to about 45°. For some designs the angle will be at least about 8° or 10°, and other designs have an angle within the range of from about 10° to about 18°. This lens geometry permits the shield to be mounted such that the mechanical centerline extends at an angle with respect to the wearer's straight-ahead normal line of sight in the as-worn orientation but the optical centerline remains generally parallel to the wearer's straight-ahead normal line of sight in the as-worn orientation.

A shield having the geometry described above can then be oriented and mounted in the support structure in any of a wide variety of manners well understood for each respective type of support structure. For example, football helmet shields may be held into place using snap-fits, screws, adhesives, interlocking structures or any of a variety of other attachment means. Shields for use in goggles or swim masks may be fit within gaskets inside annular recesses provided for that purpose, as well as other retention systems which will be well understood by those of skill in the art.

Although the foregoing invention has been described in terms of certain preferred embodiments, other embodiments will become apparent to those of ordinary skill in the art in view of the disclosure herein. Accordingly, the present invention is not intended to be limited by the recitation of preferred embodiments, but is intended to be defined solely by reference to the appended claims.

What is claimed:

1. A method of orienting a shield in a support for holding the shield in a wearer's field of vision, comprising the steps of:
   providing a support for holding a shield in the wearer's field of vision, said support configured to maintain the shield in a predetermined relationship with respect to the wearer's theoretical straight ahead line of sight;
   providing a shield having a first surface with a first center of curvature in at least a vertical plane and a second surface with a second center of curvature in at least a vertical plane, the shield defining an optical centerline, extending between the first center and the second center, and a mechanical centerline; and
   mounting the shield to the support with upward rake and such that any angle between the optical centerline and the theoretical straight ahead line of sight is no more than about 4 degrees,
wherein the optical centerline is rotated downwardly with respect to the mechanical centerline at a deviation angle of at least about 4 degrees.

2. The method of claim 1, wherein the deviation angle between the optical centerline and the mechanical centerline is at least about 8 degrees.

3. The method of claim 1, wherein the deviation angle between the optical centerline and the mechanical centerline is related to a degree of rake, such that the shield is optically correct as mounted.

4. The method of claim 1, wherein the shield is generally toroidal, with a vertical radius of curvature greater than a horizontal radius of curvature.

5. The method of claim 4, wherein the vertical radius is greater than 1.10 times the horizontal radius.

6. The method of claim 1, wherein the shield has a spherical curvature.

7. The method of claim 1, wherein the shield comprises a unitary shield extending across the wearer's left and right eyes as mounted in the wearer's field of vision.

8. The method of claim 7, wherein the shield has a horizontal arc length between about 6 inches and about 14 inches.

9. The method of claim 8, wherein the shield has a horizontal arc length between about 8 inches and about 12 inches.

10. The method of claim 7, wherein the shield has a horizontal curvature between about 3 base and 6 base.

11. The method of claim 7, wherein the deviation angle between the optical centerline and the mechanical centerline is greater than about 5°.

12. The method of claim 11, wherein the deviation angle between the optical centerline and the mechanical centerline is between about 5° and 45°.

13. The method of claim 7, wherein the deviation angle between the optical centerline and the mechanical centerline is greater than about 10°.

14. The method of claim 11, wherein the deviation angle between the optical centerline and the mechanical centerline is between about 10° and 18°.

15. The method of claim 7, wherein the optical centerline is vertically displaced from the normal line of sight by between about 0.25 inch and 0.75 inch.

16. A method of orienting a shield in a support for holding the shield in a wearer's field of vision, comprising the steps of:

providing a support for holding a shield in the wearer's field of vision, said support configured to maintain the shield in a predetermined relationship with respect to the wearer's theoretical straight ahead line of sight;

providing a shield having a first surface with a first center of curvature in at least a vertical plane and a second surface with a second center of curvature in at least a vertical plane, the shield defining an optical centerline, extending between the first center and the second center, and a mechanical centerline; and mounting the shield to the support with upward rake and such that any angle between the optical centerline and the theoretical straight ahead line of sight is no more than about 4 degrees, wherein providing a support comprises providing a safety helmet, a goggle, or an eyeglass frame, wherein the optical centerline is rotated downwardly with respect to the mechanical centerline at a deviation angle of at least about 4 degrees.

17. The method of claim 16, wherein the deviation angle between the optical centerline and the mechanical centerline is at least about 8 degrees.

18. The method of claim 16, wherein the deviation angle between the optical centerline and the mechanical centerline is related to a degree of rake, such that the shield is optically correct as mounted.

19. The method of claim 16, wherein the shield has a toroidal curvature with a vertical radius of curvature greater than a horizontal radius of curvature.

20. The method of claim 19, wherein the vertical radius is greater that 1.10 times the horizontal radius.

21. The method of claim 16, wherein the shield has a spherical curvature.

* * * * *